United States Patent
Levy

(10) Patent No.: US 11,752,154 B2
(45) Date of Patent: Sep. 12, 2023

(54) PHARMACEUTICAL COMPOSITIONS COMPRISING SEPIAPTERIN AND USES THEREOF

(71) Applicant: PTC Therapeutics MP, Inc., South Plainfield, NJ (US)

(72) Inventor: Daniel E. Levy, San Mateo, CA (US)

(73) Assignee: PTC Therapeutics MP, Inc., South Plainfield, NJ (US)

( * ) Notice: Subject to any disclaimer, the term of this patent is extended or adjusted under 35 U.S.C. 154(b) by 0 days.

(21) Appl. No.: 16/670,362

(22) Filed: Oct. 31, 2019

(65) Prior Publication Data

US 2020/0061070 A1    Feb. 27, 2020

Related U.S. Application Data

(63) Continuation of application No. PCT/US2018/049359, filed on Sep. 4, 2018.

(60) Provisional application No. 62/678,069, filed on May 30, 2018, provisional application No. 62/553,603, filed on Sep. 1, 2017.

(51) Int. Cl.
| | | |
|---|---|---|
| *A61K 31/519* | (2006.01) | |
| *A61P 25/00* | (2006.01) | |
| *A61K 9/14* | (2006.01) | |
| *A61K 9/20* | (2006.01) | |
| *A61K 38/40* | (2006.01) | |

(52) U.S. Cl.
CPC .............. *A61K 31/519* (2013.01); *A61K 9/14* (2013.01); *A61K 9/20* (2013.01); *A61K 38/40* (2013.01); *A61P 25/00* (2018.01)

(58) Field of Classification Search
CPC .................................................. A61K 31/519
USPC ....................................................... 514/249
See application file for complete search history.

(56) References Cited

U.S. PATENT DOCUMENTS

| | | |
|---|---|---|
| 4,758,571 A | 7/1988 | Curtius et al. |
| 4,774,244 A | 9/1988 | Curtius et al. |
| 5,736,343 A | 4/1998 | Landry |
| 7,566,462 B2 | 7/2009 | Jungles et al. |
| 7,566,714 B2 | 7/2009 | Oppenheimer et al. |
| 7,582,799 B2 | 9/2009 | Yoshino et al. |
| 7,612,073 B2 | 11/2009 | Oppenheimer et al. |
| 7,727,987 B2 | 6/2010 | Moser et al. |
| 7,732,599 B2 | 6/2010 | Moser et al. |
| 7,947,681 B2 | 5/2011 | Oppenheimer et al. |
| 8,003,126 B2 | 8/2011 | Jungles et al. |
| 8,067,416 B2 | 11/2011 | Oppenheimer et al. |
| 8,188,043 B2 | 5/2012 | Cooke et al. |
| 8,222,422 B2 | 7/2012 | Hashimoto et al. |
| RE43,797 E | 11/2012 | Oppenheimer et al. |
| 8,318,745 B2 | 11/2012 | Moser et al. |
| 8,410,264 B2 | 4/2013 | Dai et al. |
| 9,181,254 B2 | 11/2015 | Yoshino et al. |
| 9,212,183 B2 | 12/2015 | Sieger et al. |
| 9,433,624 B2 | 9/2016 | Oppenheimer et al. |
| 9,492,451 B2 | 11/2016 | Rustomjee et al. |
| 9,993,481 B2 | 6/2018 | Oppenheimer et al. |
| 11,072,614 B2 | 7/2021 | Levy |
| 11,130,760 B2 | 9/2021 | Yoshino et al. |
| 11,173,158 B2 | 11/2021 | Hasegawa et al. |
| 2006/0040946 A1 | 2/2006 | Oppenheimer et al. |
| 2007/0270581 A1 | 11/2007 | Jungles et al. |
| 2008/0075666 A1 | 3/2008 | Dudley et al. |
| 2010/0130500 A1 | 5/2010 | Kakkis |
| 2011/0144117 A1 | 6/2011 | Widmann et al. |
| 2013/0108694 A1 | 5/2013 | Chou et al. |
| 2013/0237543 A1 | 9/2013 | Oppenheimer et al. |
| 2013/0336975 A1 | 12/2013 | Dutzar et al. |
| 2018/0078557 A1 | 3/2018 | Hasegawa et al. |
| 2019/0308975 A1 | 10/2019 | Levy |
| 2020/0009145 A1 | 1/2020 | Hasegawa et al. |
| 2020/0010469 A1 | 1/2020 | Yoshino et al. |
| 2021/0161901 A1 | 6/2021 | Smith et al. |
| 2021/0220363 A1 | 7/2021 | Smith et al. |
| 2021/0269443 A1 | 9/2021 | Levy et al. |
| 2021/0300930 A1 | 9/2021 | Levy |
| 2022/0081443 A1 | 3/2022 | Yoshino et al. |

FOREIGN PATENT DOCUMENTS

| | | |
|---|---|---|
| CN | 1905863 A | 1/2007 |
| CN | 101132776 A | 2/2008 |
| CN | 101678025 A | 3/2010 |
| CN | 104736539 A | 6/2015 |
| JP | S59-25323 A | 2/1984 |
| JP | 2007-511536 A | 5/2007 |
| JP | 2008-520574 A | 6/2008 |
| JP | 2010-523708 A | 7/2010 |

(Continued)

OTHER PUBLICATIONS

Bernegger et al., "High frequency of tetrahydrobiopterin-responsiveness among hyperphenylalaninemias: a study of 1,919 patients observed from 1988 to 2002," Mol Genet Metab. 77(4): 304-13 (2002).

Blau et al., "Tetrahydrobiopterin deficiencies without hyperphenylalaninemia: diagnosis and genetics of DOPA-responsive dystonia and sepiapterin reductase deficiency," Mol Genet Metab. 74(1-2): 172-85 (2001).

Curtius et al., "Atypical phenylketonuria due to tetrahydrobiopterin deficiency. Diagnosis and treatment with tetrahydrobiopterin, dihydrobiopterin and sepiapterin," Clin Chim Acta. 93(2): 251-62 (1979).

Grant et al., "Relationships among rat ultrasonic vocalizations, behavioral measures of striatal dopamine loss, and striatal tyrosine hydroxylase immunoreactivity at acute and chronic time points following unilateral 6-hydroxydopamine-induced dopamine depletion," available in PMC Sep. 15, 2016, published in final edited form as: Behav Brain Res. 291:361-71 (2015) (24 pages).

(Continued)

*Primary Examiner* — Taofiq A Solola
(74) *Attorney, Agent, or Firm* — Clark & Elbing LLP

(57) ABSTRACT

The present invention features pharmaceutical compositions including sepiapterin, or a pharmaceutically acceptable salt and/or co-crystal thereof, and methods for the treatment of tetrahydrobiopterin-related disorders (e.g., tetrahydrobiopterin deficiency or phenylketonuria) with such compositions.

20 Claims, 16 Drawing Sheets

(56) References Cited

FOREIGN PATENT DOCUMENTS

| | | |
|---|---|---|
| JP | 2011-530540 A | 12/2011 |
| JP | 2012-207029 A | 10/2012 |
| JP | 2013-502396 A | 1/2013 |
| JP | 2014-15477 A | 1/2014 |
| JP | 2019-535836 A | 12/2019 |
| WO | WO-2005/028462 A1 | 3/2005 |
| WO | WO-2005/049000 A2 | 6/2005 |
| WO | WO-2008/128049 A2 | 10/2008 |
| WO | WO-2010/072776 A1 | 7/2010 |
| WO | WO-2011/132435 A1 | 10/2011 |
| WO | WO-2013/168693 A1 | 11/2013 |
| WO | WO2018/019931 A1 * | 2/2018 |
| WO | WO-2018/102314 A1 | 6/2018 |
| WO | WO-2018/102315 A1 | 6/2018 |
| WO | WO-2018/195321 A1 | 10/2018 |
| WO | WO-2019/046849 A1 | 3/2019 |
| WO | WO-2021/026247 A1 | 2/2021 |
| WO | WO-2021/062264 A1 | 4/2021 |

OTHER PUBLICATIONS

Hennermann et al., "Partial and total tetrahydrobiopterin-responsiveness in classical and mild phenylketonuria (PKU)," J Inherit Metab Dis. 25(Suppl 1): 21:042-P (2002) (Abstract only).
Ichiyama et al., "Enzymic studies on the biosynthesis of serotonin in mammalian brain," J Biol Chem. 245(7): 1699-709 (1970).
International Search Report and Written Opinion for International Application No. PCT/US18/49359, dated Nov. 15, 2018 (11 pages).
Kaufman, "Phenylalanine hydroxylation cofactor in phenylketonuria," Science. 128(3337): 1506-8 (1958).
Klaiman et al., "Tetrahydrobiopterin as a treatment for autism spectrum disorders: a double-blind, placebo-controlled trial," J Child Adolesc Psychopharmacol. 23(5): 320-8 (2013) (11 pages).
Kure et al., "Tetrahydrobiopterin-responsive phenylalanine hydroxylase deficiency," J Pediatr. 135(3): 375-8 (1999).
Kwon et al., "Reduced biopterin as a cofactor in the generation of nitrogen oxides by murine macrophages," J Biol Chem. 264(34): 20496-501 (1989).
Matalon et al., "Tetrahydrobiopterin ($BH_4$) responsive phenylalanine hydroxylase (PAH) mutations," J Inherit Metab Dis. 25(Suppl 1): 23:045-P (2002) (Abstract only).
Mayer et al., "Brain nitric oxide snythase is a biopterin- and flavin-containing multi-functional oxido-reductase," FEBS Lett. 288(1-2): 187-91 (1991).
Muntau et al., "Tetrahydrobiopterin as an alternative treatment for mild phenylketonuria," N Engl J Med. 347(26): 2122-32 (2002).
Nagatsu et al., "Tyrosine hydroxylase. The initial step in norepinephrine biosynthesis," J Biol Chem. 239(9): 2910-7 (1964).
Niederwieser et al., "Atypical phenylketonuria with defective biopterin metabolism. Monotherapy with tetrahydrobiopterin or sepiapterin, screening and study of biosynthesis in man," Eur J Pediatr. 138(2): 110-2 (1982).
Pfleiderer et al., "Pteridine, LXVIII. Überführung von biopterin in sepiapterin und absolute konfiguration des sepiapterins," Chem Ber. 112: 2750-2755 (1979).
Sawabe et al., "Cellular uptake of sepiapterin and push-pull accumulation of tetrahydrobiopterin," Mol Genet Metab. 94(4): 410-6 (2008).
Sawabe et al., Sepiapterin administration raises tissue BH4 levels more efficiently than $BH_4$ supplement in normal mice, *Chemistry and Biology of Pteridines and Folates*. Ed. Milstien et al., pp. 199-204 (2001).
Schircks et al., "Über Pterinchemie. 65 Mitteilung [1]. Herstellung von (6 R,S)-5,6,7,8-Tetrahydro-L-biopterin, 7,8-Dihydro-L-biopterin, L-Sepiapterin, Deoxysepiapterin, (6 R,S)-5,6-Dihydrodeoxysepiapterin and 2'-Deoxybiopterin," Helv Chim Acta. 61(7): 2731-8 (1978).
Spaapen et al., "Tetrahydrobiopterin-responsive phenylalanine hydroxylase deficiency, state of the art," Mol Genet Metab. 78(2): 93-9 (2003).
Sugiura et al., "The structures of the reoxidation products of 7,8-dihydroneopterin," Bull Chem Soc Jpn. 46(3): 939-42 (1973).
Tietz et al., "A new pteridine-requiring enzyme system for the oxidation of glyceryl ethers," J Biol Chem. 239(12): 4081-90 (1964).
Shircks Laboratories, "Data Sheet: L-Sepiapterin. Product No. 11.225," published Jan. 26, 2016 (1 page).
Ponzone et al., "Hyperphenylalaninemia and pterin metabolism in serum and erythrocytes," Clin Chim Acta. 216(1-2): 63-71 (1993).
Balbach et al., "Pharmaceutical evaluation of early development candidates 'the 100 mg-approach'," Int J Pharm. 275(1-2):1-12 (2004).
Calra, "Crystalline polymorphism of organic compounds," Topics In Current Chemistry. 198:163-208 (1998).
Clinical Trials "A Study of CNSA-001 in Primary Tetrahydrobiopterin (BH4) Deficient Participants with Hyperphenylalaninemia," (printed on Feb. 11, 2021).
NORD "Tetrahydrobiopterin Deficiency," (online PD Sep. 2016).
Singhal et al., "Drug polymorphism and dosage form design: a practical perspective." Adv Drug Deliv Rev. 56(3): 335-47 (2004).
U.S. Appl. No. 17/059,632, PTC Therapeutics MP, Inc.
U.S. Appl. No. 17/059,719, PTC Therapeutics MP, Inc.
U.S. Appl. No. 17/059,887, PTC Therapeutics MP, Inc.
Brittain et al., "Polymorphism In Pharmaceutical Solids," CRC Press. 192:3-480 (2016).
Kuplennik et al., "Enhanced nanoencapsulation of sepiapterin within PEG-PCL nanoparticles by complexation with triacetyl-beta cyclodextrin," Molecules. 24: 2715 (2019).
Park et al., "Optimization of expression conditions enhances production of sepiapterin, a precursor for tetrahydrobiopterin biosynthesis, in recombinant *Escherichia coli*," J Microbiol Biotechnol. 25(10): 1709-13 (2015).
Saeed et al., "Uncertainty of thermal characterization of phase change material by differential scanning calorimetry analysis," Int J Eng Res Technol. 5(1): 405-12 (2016).
Schircks et al., "Herstellung von (6 R, S)-5,6,7,8-Tetrahydro-L-biopterin, 7,8-Dihydro-L-biopterin, L-Sepiapterin, Deoxysepiapterin, (6 R, S)-5,6-Dihydrodeoxysepiapterin und 2'-Deoxybiopterin," Helvetica Chimica Acta. 61(7): 2731-2738 (1978).
Smith et al., "Phase I clinical evaluation of CNSA-001 (sepiapterin), a novel pharmacological treatment for phenylketonuria and tetrahydrobiopterin deficiencies, in healthy volunteers," Mol Genet Metab. 126(4): 406-12 (2019).
Viscontini et al., "Fluorescent substances from Drosophilia melanogaster. XII. The yellow fluorescent pterine: sepiapterin and isosepiapterin," Helvetica Chimica Acta. 42:836-41 (1959).
Woo et al., "Production of sepiapterin in *Escherichia coli* by coexpression of cyanobacterial GTP cyclohydrolase I and human 6-pyruvoyltetrahydropterin synthase," Applied and Environmental Microbiology. 68(6): 3138-3140 (2002).
Shircks Laboratories, "Data Sheet: Tetrahydrobioterin Tablets," published Jul. 1, 2009 (1 page).
Opladen et al., "Consensus guideline for the diagnosis and treatment of tetrahydrobiopterin ($BH_4$) deficiencies." Orphanet J Rare Dis. 15(1):126 (2020) (30 pages).
U.S. Appl. No. 17/342,910, PTC Therapeutics MP, Inc.
U.S. Appl. No. 17/486,421, PTC Therapeutics MP, Inc.
Abell et al., "Effect of oral CNSA-001 (sepiapterin, PTC923) on gastric accommodation in women with diabetic gastroparesis: a randomized, placebo-controlled, phase 2 trial," J Diabetes Complications. 35(9):107961 (2021) (7 pages).
Bratkovic et al., "PTC923 (sepiapterin) lowers elevated blood phenylalanine in subjects with phenylketonuria: a phase 2 randomized, multi-center, three-period crossover, open-label, active controlled, all-comers study," Metabolism. 128:155116 (2022) (8 pages).
Office Action for Japanese Patent Application No. 2019-548533, dated Oct. 26, 2021 (10 pages).
Office Action for Japanese Patent Application No. 2019-548534, dated Nov. 2, 2021 (10 pages).

(56) References Cited

OTHER PUBLICATIONS

Ono, "Analysis of salt selection of current active pharmaceutical ingredients (API)," Yakuzaigaku. 73(3):176-182 (2013) (8 pages).
Smith et al., "Exploratory study of the effect of one week of orally administered CNSA-001 (sepiapterin) on CNS levels of tetrahydrobiopterin, dihydrobiopterin and monoamine neurotransmitter metabolites in healthy volunteers," Mol Genet Metab Rep. 21:100500 (2019) (3 pages).
Takada, "API form screening and selection in drug discovery stage," Pharm Stage. 6(10):20-25 (2007) (9 pages).
Yoshinaki, *Organic compound crystal production handbook.* 10-11, 57-73, 78-81 (2008) (13 pages).

* cited by examiner

FIG. 1

| Group Number | Animal Number | Protocol Timepoint (hours) | Run One (Sepiapterin, nM) | Run Two (Sepiapterin, nM) | Run One (Sepiapterin, nM) | Run Two (Sepiapterin, nM) | Mean (Sepiapterin, nM) |
|---|---|---|---|---|---|---|---|
| | | | Raw Data | | Adjusted for dilution | | |
| 1 | 1 | 1 | 39.9 | 43.5 | 46.6 | 50.7 | 48.6 |
| 1 | 2 | 1 | 62.4 | 59.1 | 72.7 | 68.9 | 70.8 |
| 1 | 3 | 1 | 89.3 | 95.3 | 104.2 | 111.1 | 107.7 |
| 1 | 4 | 4 | 34.6 | 38.6 | 40.3 | 45.1 | 42.7 |
| 1 | 5 | 4 | 32.7 | 29.8 | 38.1 | 34.8 | 36.5 |
| 1 | 6 | 4 | 39.3 | 38.4 | 45.8 | 44.8 | 45.3 |
| 1 | 7 | 8 | 8.3 | 10.4 | 9.6 | 12.1 | 10.9 |
| 1 | 8 | 8 | 42.8 | 43.0 | 49.9 | 50.2 | 50.1 |
| 2 | 10 | 1 | 71.7 | 73.9 | 83.7 | 85.0 | 84.4 |
| 2 | 11 | 1 | 109.9 | 108.8 | 128.2 | 126.9 | 127.6 |
| 2 | 12 | 1 | 81.0 | 81.7 | 94.4 | 95.3 | 94.9 |
| 2 | 13 | 4 | 18.3 | 20.4 | 21.4 | 23.8 | 22.6 |
| 2 | 14 | 4 | 65.4 | 64.9 | 76.3 | 75.8 | 76.0 |
| 2 | 15 | 4 | 37.2 | 39.1 | 43.3 | 45.6 | 44.5 |
| 2 | 16 | 8 | 18.6 | 19.0 | 21.7 | 22.2 | 22.0 |
| 2 | 17 | 8 | 20.5 | 19.6 | 23.9 | 22.9 | 23.4 |
| 2 | 18 | 8 | 59.6 | 60.8 | 69.5 | 70.9 | 70.2 |

FIG. 3

| Treatment | Group Number (Dose Level) | Analyte | BH4 | | | Sepiapterin | | | |
|---|---|---|---|---|---|---|---|---|---|
| | | Matrix | Kidney | Liver | Urine | Kidney | Liver | Urine | Plasma |
| BH4 | 1 (20 mg/kg) | $T_{max}$ | 1.00 | 1.00 | 4.00 | | | | |
| | | $C_{max}$ | 3.42 | 2.36 | 385 | | | | |
| | | $T_{last}$ | 8.00 | 8.00 | 8.00 | | | | |
| | | $C_{last}$ | 0.426 | 1.59 | 252 | | | | |
| | | $t_{1/2}$ | NA | NA | NA | | | | |
| | | $AUC_{last}$ | 8.83 | 14.9 | 2100 | | | | |
| BH4 | 2 (60 mg/kg) | $T_{max}$ | 1.00 | 1.00 | 4.00 | | | | |
| | | $C_{max}$ | 8.55 | 4.89 | 1040 | | | | |
| | | $T_{last}$ | 8.00 | 8.00 | 8.00 | | | | |
| | | $C_{last}$ | 0.733 | 1.81 | 604 | | | | |
| | | $t_{1/2}$ | 2.58 | NA | NA | | | | |
| | | $AUC_{last}$ | 23.6 | 23.3 | 6060 | | | | |
| BH4 | 3 (180 mg/kg) | $T_{max}$ | 2.00 | 2.00 | 8.00 | | | | |
| | | $C_{max}$ | 14.8 | 11.8 | 1400 | | | | |
| | | $T_{last}$ | 8.00 | 8.00 | 8.00 | | | | |
| | | $C_{last}$ | 1.81 | 2.47 | 1400 | | | | |
| | | $t_{1/2}$ | NA | NA | NA | | | | |
| | | $AUC_{last}$ | 47.2 | 38.6 | 9980 | | | | |
| Sepiapterin | 4 (20 mg/kg) | $T_{max}$ | 2.00 | 0.50 | 4.00 | 0.50 | | 8.00 | 2.00 |
| | | $C_{max}$ | 4.62 | 9.46 | 592 | 0.0980 | | 171 | 9.29 |
| | | $T_{last}$ | 8.00 | 8.00 | 8.00 | 0.50 | | 8.00 | 8.00 |
| | | $C_{last}$ | 0.364 | 1.92 | 470 | 0.0980 | | 171 | 1.56 |
| | | $t_{1/2}$ | NA | NA | NA | NA | | NA | NA |
| | | $AUC_{last}$ | 20.5 | 32.9 | 3400 | 0.0245 | | 1020 | 26.7 |
| Sepiapterin | 5 (60 mg/kg) | $T_{max}$ | 0.50 | 2.00 | 2.00 | 0.50 | 0.50 | 0.50 | 0.50 |
| | | $C_{max}$ | 9.72 | 13.8 | 880 | 0.281 | 0.271 | 312 | 28.8 |
| | | $T_{last}$ | 8.00 | 8.00 | 8.00 | 0.50 | 0.50 | 4.00 | 8.00 |
| | | $C_{last}$ | 1.34 | 2.48 | 89.9 | 0.281 | 0.271 | 171 | 6.28 |
| | | $t_{1/2}$ | 2.47 | NA | NA | NA | NA | NA | NA |
| | | $AUC_{last}$ | 35.6 | 63.1 | 3530 | 0.0702 | 0.0678 | 706 | 85.9 |
| Sepiapterin | 6 (180 mg/kg) | $T_{max}$ | 1.00 | 2.00 | 2.00 | 0.50 | 0.50 | 0.50 | 0.50 |
| | | $C_{max}$ | 31.5 | 26.6 | 1540 | 4.44 | 19.3 | 1120 | 439 |
| | | $T_{last}$ | 8.00 | 8.00 | 8.00 | 0.50 | 0.50 | 2.00 | 8.00 |
| | | $C_{last}$ | 3.13 | 4.12 | 144 | 4.44 | 19.3 | 364 | 24.3 |
| | | $t_{1/2}$ | NA | NA | NA | NA | NA | NA | NA |
| | | $AUC_{last}$ | 73.1 | 112 | 8110 | 1.11 | 4.83 | 1400 | 898 |

PHARMACEUTICAL COMPOSITIONS COMPRISING SEPIAPTERIN AND USES THEREOF

BACKGROUND OF THE INVENTION

Primary tetrahydrobiopterin deficiency (PBD) is caused by deficiency of GTP cyclohydrolase I (GTP-CH), 6-pyruvoyl-tetrahydropterin synthase (PTPS), or sepiapterin reductase (SR) that impair the biosynthesis of tetrahydrobiopterin (BH4) or by defects in BH4 recycling (pterin-4a-carbinolamine dehydratase (PCD) or dihydropteridine reductase (DHPR) deficiency). PBD accounts for 1 to 3% of all cases of hyperphenylalaninemia (HPA), with virtually all of the remaining cases due to phenylalanine hydroxylase deficiency.

BH4 is an essential cofactor for phenylalanine hydroxylase, tyrosine hydroxylase, tryptophan hydroxylase, fatty acid glycerylether oxygenase, and nitric oxide (NO) synthase.

In PBD, impaired hydroxylation of Phenylalanine (Phe) to Tyrosine (Tyr) results in HPA. The reduced synthesis of Tyr and impaired activities of Tyr and tryptophan hydroxylases results in reduced formation of neurotransmitters and consequent neuromotor deficits.

Phenotypically, BH4 deficiency presents with HPA and deficiency of the neurotransmitter precursors, L-dopa and 5-hydroxytryptophan, and thus may be detected through screening programs which measure Phe in order to detect phenylalanine hydroxylase deficiency (the exception being SR deficient patients who have normal Phe concentrations).

Current treatment of BH4 deficiency consists of reducing Phe concentrations in blood either by oral administration of BH4 (in GTP-CH and PTPS deficiency) and/or low Phe diet (mainly in DHPR deficiency) and administration of the neurotransmitter precursors L-dopa and 5-hydroxytryptophan (5HTP).

Reports of long-term follow-up of patients with BH4 deficiency are scarce. Therapeutic strategies vary by treating physician and clinic, are far from clinically based evidence, and include pharmacologic agents none of which have marketing approval for this indication. Therefore, a need exists for new therapies for BH4 deficiency.

SUMMARY OF THE INVENTION

The present invention features pharmaceutical compositions including sepiapterin, or a pharmaceutically acceptable salt and/or co-crystal thereof, and methods for the treatment of tetrahydrobiopterin-related disorders with such compositions.

Accordingly, in an aspect, the invention features a pharmaceutical composition including sepiapterin, or a pharmaceutically acceptable salt and/or co-crystal thereof, wherein the pharmaceutical composition is stable at room temperature (e.g., 25° C. or 25° C. and 60% relative humidity) for at least 6 months. For example, the level of sepiapterin, or a pharmaceutically acceptable salt and/or co-crystal thereof, in the composition decreases by less than 5% (e.g., less than 4%, less than 3%, less than 2%, less than 1%) when the composition is stored at room temperature for 6 months and/or the level of lactoylpterin in the composition increases by less than 5% (e.g., less than 4%, less than 3%, less than 2%, or less than 1%) when the composition is stored at room temperature for 6 months.

In some embodiments, the pharmaceutical composition is a solid composition (e.g., a powder, a capsule, or a tablet). In some embodiments, the pharmaceutical composition is formulated for use in a suspension.

In some embodiments, the pharmaceutical composition further comprises an antioxidant. In some embodiments, the antioxidant is present in an amount sufficient to stabilize the sepiapterin, or a pharmaceutically acceptable salt and/or co-crystal thereof, in the composition for at least 6 months at room temperature (e.g., 25° C. or 25° C. and 60% relative humidity).

In an aspect, the invention features a solid pharmaceutical composition of sepiapterin, or a pharmaceutically acceptable salt and/or co-crystal thereof and an antioxidant. In some embodiments, the antioxidant is present in an amount sufficient to stabilize the sepiapterin, or a pharmaceutically acceptable salt and/or co-crystal thereof, in the composition for at least 6 months at room temperature (e.g., 25° C. or 25° C. and 60% relative humidity).

In an aspect, the invention features a pharmaceutical composition including sepiapterin, or a pharmaceutically acceptable salt and/or co-crystal thereof, and an antioxidant (e.g., ascorbic acid), wherein the ratio of sepiapterin, or a pharmaceutically acceptable salt and/or co-crystal thereof, to antioxidant is greater than 4:1 (e.g., greater than 5:1, greater than 6:1, greater than 7:1, greater than 8:1, greater than 9:1, greater than 10:1, greater than 15:1, greater than 20:1) wt/wt.

In an aspect, the invention features a pharmaceutical composition including sepiapterin, or a pharmaceutically acceptable salt and/or co-crystal thereof, and an antioxidant, wherein the pharmaceutical composition includes more sepiapterin, or pharmaceutically acceptable salt and/or co-crystal thereof, than antioxidant by weight. For example, in some embodiments, the sepiapterin, or pharmaceutically acceptable salt and/or co-crystal thereof, and antioxidant (e.g., ascorbic acid) are present in a ratio of at least 1:1 (e.g., 2:1, 3:1, 4:1, 5:1, 6:1, 7:1, 8:1, 9:1, or 10:1) wt/wt.

In some embodiments, the composition is a solid pharmaceutical composition of sepiapterin, or a pharmaceutically acceptable salt and/or co-crystal thereof and an antioxidant. In some embodiments, the antioxidant is present in an amount sufficient to stabilize the sepiapterin, or a pharmaceutically acceptable salt and/or co-crystal thereof, in the composition for at least 6 months at room temperature (e.g., 25° C. or 25° C. and 60% relative humidity). In some embodiments, the ratio of sepiapterin, or a pharmaceutically acceptable salt and/or co-crystal thereof, to antioxidant is greater than 4:1 (e.g., greater than 5:1, greater than 6:1, greater than 7:1, greater than 8:1, greater than 9:1, greater than 10:1, greater than 15:1, greater than 20:1) wt/wt.

In an aspect, the invention features a pharmaceutical composition including sepiapterin, or a pharmaceutically acceptable salt and/or co-crystal thereof, and less than 10% (e.g., less than 9%, less than 8%, less than 7%, less than 6%, less than 5%, less than 4%, less than 3%, less than 2%, or less than 1%) antioxidant (e.g., ascorbic acid) by total weight. In some embodiments, the pharmaceutical composition is substantially free of antioxidant.

In an aspect, the invention features a pharmaceutical composition including sepiapterin, or a pharmaceutically acceptable salt and/or co-crystal thereof, and less than 50% (e.g., less than 40%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, or less than 0.2%) lactoylpterin by weight of the combined amount of sepiapterin, or salt and/or co-crystal thereof, and lactoylpterin in the composition. In some embodiments, the pharmaceutical composition includes less than 10% lactoylpterin. In some embodiments, the pharmaceutical composition includes less than 1.3% lactoylpterin. In some embodiments, the pharmaceutical composition further includes an antioxidant (e.g., ascorbic acid). In other embodiments, the pharmaceutical composition does not include an antioxidant.

In an aspect, the invention features a particulate pharmaceutical composition including sepiapterin, or a pharmaceutically acceptable salt and/or co-crystal thereof, and an antioxidant (e.g., ascorbic acid), e.g., for use in a suspension.

In an aspect, the invention features a pharmaceutical composition formulated as a suspension in a dosing vehicle including a bulking agent or anti-caking agent, sepiapterin, or pharmaceutically acceptable salt thereof, and an antioxidant, wherein at least 50% (e.g., at least 60%, at least 70%, at least 80%, at least 90%, at least 95%, or at least 99%) of the sepiapterin, or pharmaceutically acceptable salt and/or co-crystal thereof, is dissolved in the dosing vehicle.

In an aspect, the invention features a pharmaceutical composition formulated as a suspension in a dosing vehicle including a bulking agent or anti-caking agent, sepiapterin, or a pharmaceutically acceptable salt and/or co-crystal thereof, and an antioxidant, wherein the concentration of sepiapterin, or a pharmaceutically acceptable salt and/or co-crystal thereof, in the dosing vehicle is 1 mg/mL to 5 mg/mL (e.g., at least 1 mg/mL, at least 1.1 mg/mL, at least 1.2 mg/mL, at least 1.3 mg/mL, at least 1.4 mg/mL, at least 1.5 mg/ml, at least 1.6 mg/mL, at least 1.7 mg/mL, at least 1.8 mg/mL, at least 1.9 mg/mL, at least 2.0 mg/mL, or at least 2.1 mg/ml).

In an aspect, the invention features a pharmaceutical composition formulated as a suspension in a dosing vehicle including a bulking agent or anti-caking agent, sepiapterin, or a pharmaceutically acceptable salt and/or co-crystal thereof, and an antioxidant, wherein at least 50% (e.g., at least 60%, at least 70%, at least 80%, at least 90%, at least 95%, or at least 99%) of the sepiapterin, or a pharmaceutically acceptable salt and/or co-crystal thereof, is adsorbed on the bulking or anti-caking agent.

In some embodiments of any of the foregoing pharmaceutical compositions, the antioxidant is 4-chloro-2,6-ditert-butylphenol, tocopherol, alpha-tocopherol, alkylated diphenylamines, ascorbic acid, ascorbyl myristate, ascorbyl palmitate, ascorbyl stearate, beta-carotene, butylated hydroxyanisole, butylated hydroxytoluene, citric acid, cysteine, D-alpha-tocopheryl polyethylene glycol 1000 succinate, deferoxamine methanesulfonate, dodecyl gallate, ethylparaben, folic acid, fumaric acid, gallic acid, glutathione, lecithin, malic acid, methylparaben, monothioglycerol, N-acetyl cysteine, nordihydroguaiaretic acid, octyl gallate, p-phenylenediamine, potassium ascorbate, potassium metabisulfite, potassium sorbate, propionic acid, propyl gallate, retinol, sorbic acid, sodium ascorbate, sodium bisulfite, sodium hydrosulfite, sodium isoascorbate, sodium metabisulfite, sodium sulfite, sodium thiosulfate, tartaric acid, tert-butylhydroquinone, tocopheryl acetate, vitamin A, vitamin B6, vitamin B12, or vitamin E, or a combination thereof. In some embodiments of any of the foregoing pharmaceutical compositions, the antioxidant is ascorbic acid, tocopherol, retinol, ascorbyl palmitate, N-acetyl cysteine, glutathione, butylatedhydroxytoluene, and/or butylatedhydroxyanisole.

In some embodiments of any of the foregoing compositions, the pharmaceutical composition includes about 20-95% (e.g., about 20%, about 21%, about 22%, about 23%, about 24%, about 25%, about 26%, about 27%, about 28%, about 29%, about 30%, about 40%, about 50%, about 60%, about 70%, about 80%, about 90%, about 95% or about 20-30%, about 25-45%, about 40-60%, about 50-75%, about 65-75%, about 70-90%, about 85-95%) sepiapterin, or a pharmaceutically acceptable salt and/or co-crystal thereof, by total weight.

In some embodiments of any of the foregoing compositions, the pharmaceutical composition further includes a dispersant (e.g., a carboxymethylcellulose or a pharmaceutically acceptable salt and/or co-crystal thereof such as croscarmellose sodium). In some embodiments of any of the foregoing compositions, the pharmaceutical composition includes 0.1-1.5% (e.g., 0.1-0.3%. 0.2-0.4%, 0.3-0.5%, 0.4-0.6%, 0.5-0.7%, 0.6-0.8%, 0.7-0.9%, 0.8-1%, 0.9-1.1%, 1-1.2%, 1.1-1.3%, 1.2-1.4%, or 1.3-1.5%) dispersant (e.g., croscarmellose sodium) by total weight.

In some embodiments of any of the foregoing compositions, the pharmaceutical composition includes at least one anti-caking agent or bulking agent (e.g., a bulking agent and an anti-caking agent). In some embodiments, the at least one anti-caking agent or bulking agent is colloidal silicon dioxide or microcrystalline cellulose. In some embodiments, the pharmaceutical composition includes 60-80%, e.g., 65-75%, (e.g., about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, or about 80%) anti-caking agent and/or bulking agent by total weight. In some embodiments of any of the foregoing compositions, the pharmaceutical composition includes both colloidal silicon dioxide and microcrystalline cellulose. In some embodiments of any of the foregoing compositions, the pharmaceutical composition includes 60-65% (about 60%, about 61%, about 62%, about 63%, about 64%, or about 65%) microcrystalline cellulose by total weight and 2-15% (e.g., about 5-7%, about 2%, about 3%, about 4%, about 5%, about 6%, about 7%, about 8%, about 9%, about 10%, about 11%, about 12%, about 13%, about 14%, or about 15%) colloidal silicon dioxide by total weight.

In some embodiments of any of the foregoing compositions, sepiapterin, or a pharmaceutically acceptable salt and/or co-crystal thereof, is in crystalline form. In some embodiments, the crystalline form of sepiapterin has at least one peak at diffraction angle 2θ (°) of about 9.7°±0.5, about 10.2°±0.5, and/or about 11.3°±0.5 as measured by X-ray diffractometry by irradiation with Cu Kα X-rays or calculated from X-ray diffractometry.

In some embodiments, the crystalline form of sepiapterin is characterized by peaks at angles of refraction 2θ of at least about 9.7°, about 10.2°, about 11.3°, about 14.0°, about 14.6°, about 19.9°, about 22.2°, about 25.3°, and about 32.4°. In some embodiments, the crystalline form of sepiapterin is characterized by refractions at angles of refraction 2θ as set forth in Table 1.

TABLE 1

| 2θ(°) | Intensity |
|---|---|
| 9.7 | 98.27 |
| 10.2 | 100.00 |
| 11.3 | 22.47 |
| 14.0 | 5.01 |
| 14.6 | 12.36 |
| 19.9 | 5.63 |
| 21.1 | 3.72 |

TABLE 1-continued

| 2θ(°) | Intensity |
|---|---|
| 22.2 | 5.37 |
| 22.7 | 4.04 |
| 24.5 | 2.99 |
| 25.3 | 17.65 |
| 27.2 | 3.10 |
| 32.4 | 5.29 |
| 36.7 | 2.72 |

In other embodiments, the crystalline form of sepiapterin has at least one peak at diffraction angle 2θ (°) of about 8.4°±0.5, 16.9°±0.5, and/or 25.4°±0.5 as measured by X-ray diffractometry by irradiation with Cu Kα X-rays or calculated from X-ray diffractometry.

In some embodiments, the crystalline form of sepiapterin is characterized by refractions at angles of refraction 2θ of at least about 8.4°, about 14.9°, about 16.9°, about 25.4°, and about 34.1°. In some embodiments, the crystalline form of sepiapterin is characterized by refractions at angles of refraction 2θ as set forth in Table 2.

TABLE 2

| 2θ(°) | Intensity |
|---|---|
| 8.4 | 100.00 |
| 14.9 | 2.34 |
| 16.9 | 10.70 |
| 25.4 | 84.90 |
| 34.1 | 3.00 |

In further embodiments, the crystalline form of sepiapterin has at least one peak at diffraction angle 2θ (°) of about 5.7°±0.5, 7.8°±0.5, and/or 25.4°±0.5 as measured by X-ray diffractometry by irradiation with Cu Kα X-rays or calculated from X-ray diffractometry.

In some embodiments, the crystalline form of sepiapterin is characterized by refractions at angles of refraction 2θ of at least about 5.7°, about 7.8°, about 9.1°, about 11.5°, about 15.3°, about 16.0°, about 20.1°, about 25.4°, and about 26.6°. In some embodiments, the crystalline form of sepiapterin is characterized by refractions at angles of refraction 2θ as set forth in Table 3.

TABLE 3

| 2θ(°) | Intensity |
|---|---|
| 5.7 | 48.91 |
| 7.8 | 100.00 |
| 9.1 | 59.49 |
| 10.4 | 8.72 |
| 11.5 | 24.53 |
| 12.9 | 8.50 |
| 14.8 | 9.24 |
| 15.3 | 12.53 |
| 16.0 | 14.09 |
| 17.2 | 7.22 |
| 18.2 | 4.25 |
| 19.2 | 5.78 |
| 20.1 | 14.54 |
| 21.5 | 6.47 |
| 22.9 | 6.85 |
| 23.7 | 4.80 |
| 25.4 | 65.68 |
| 26.6 | 14.53 |
| 27.4 | 8.39 |
| 31.5 | 3.74 |
| 34.2 | 4.36 |

In yet other embodiments, the crystalline form of sepiapterin has at least one peak at diffraction angle 2θ (°) of about 8.9°±0.5, 10.3°±0.5, and/or 26.0°±0.5 as measured by X-ray diffractometry by irradiation with Cu Kα X-rays or calculated from X-ray diffractometry.

In some embodiments, the crystalline form of sepiapterin is characterized by refractions at angles of refraction 2θ of at least about 8.9°, about 10.3°, about 10.9°, about 17.8°, about 24.9°, about 26.0°, about 26.7°, about 26.8°, and about 28.3°. In some embodiments, the crystalline form of sepiapterin is characterized by refractions at angles of refraction 2θ as set forth in Table 4.

TABLE 4

| 2θ(°) | Intensity |
|---|---|
| 8.9 | 100.00 |
| 10.3 | 49.92 |
| 10.9 | 19.96 |
| 11.6 | 2.15 |
| 13.6 | 2.99 |
| 14.2 | 3.45 |
| 14.8 | 2.35 |
| 15.4 | 2.59 |
| 16.4 | 1.55 |
| 17.2 | 2.33 |
| 17.8 | 6.24 |
| 19.6 | 2.62 |
| 20.1 | 2.28 |
| 20.5 | 3.09 |
| 20.8 | 2.27 |
| 21.3 | 3.60 |
| 22.3 | 4.79 |
| 23.7 | 4.31 |
| 24.9 | 5.19 |
| 26.0 | 41.94 |
| 26.7 | 8.58 |
| 26.8 | 9.17 |
| 27.4 | 3.98 |
| 28.3 | 4.75 |
| 28.7 | 6.60 |
| 29.8 | 3.03 |
| 31.8 | 2.72 |
| 33.0 | 2.03 |
| 35.5 | 1.57 |
| 37.1 | 1.09 |

In yet other embodiments, the crystalline form of sepiapterin has at least one peak at diffraction angle 2θ of 10.0°±0.5, 10.6°±0.5, and 25.7°±0.5.

In some embodiments, the crystalline form of sepiapterin is characterized by refractions at angles of refraction 2θ of at least 10.0°±0.5, 10.6°±0.5, 11.2°±0.5, 15.3°±0.5, 15.9°±0.5, 22.8°±0.5, 24.4°±0.5, 25.0°±0.5, 25.7°±0.5, and 26.6°±0.5 In some embodiments, the crystalline form of sepiapterin is characterized by refractions at angles of refraction 2θ as set forth in Table 5.

TABLE 5

| 2θ (°) | Intensity |
|---|---|
| 5.3 | 8.30 |
| 6.9 | 4.54 |
| 10.0 | 100.00 |
| 10.6 | 69.64 |
| 11.2 | 6.59 |
| 13.5 | 7.52 |
| 15.3 | 26.59 |
| 15.9 | 26.43 |
| 16.0 | 23.41 |
| 16.9 | 4.28 |
| 18.6 | 13.02 |
| 19.3 | 11.90 |

TABLE 5-continued

| 2θ (°) | Intensity |
|---|---|
| 20.1 | 7.22 |
| 20.8 | 11.01 |
| 22.8 | 16.77 |
| 23.5 | 19.60 |
| 24.4 | 41.45 |
| 25.0 | 23.99 |
| 25.7 | 65.40 |
| 26.6 | 39.64 |
| 27.6 | 13.04 |
| 28.7 | 6.55 |
| 30.8 | 14.76 |
| 32.2 | 9.63 |
| 33.7 | 5.16 |
| 37.5 | 5.80 |

In some embodiments of any of the foregoing compositions, sepiapterin is a pharmaceutically acceptable salt and/or co-crystal of sepiapterin. In some embodiments, the salt and/or co-crystal of sepiapterin is the methanesulfonate salt and/or co-crystal, the nicotinate salt and/or co-crystal, the p-toluenesulfonate salt and/or co-crystal, the benzenesulfonate salt and/or co-crystal, the phosphate salt and/or co-crystal (e.g., a 1:1 phosphate salt and/or co-crystal, i.e., one molecule of sepiapterin to one molecule phosphate), the malonate salt and/or co-crystal (e.g., a 1:1 malonate salt and/or co-crystal, i.e., one molecule of sepiapterin to one molecule malonate), the tartrate salt and/or co-crystal (e.g., a 1:1 tartrate salt and/or co-crystal, i.e., one molecule of sepiapterin to one molecule tartrate), the gentisate salt and/or co-crystal (e.g., a 2:1 gentisate salt and/or co-crystal, i.e., two molecules of sepiapterin to one molecule gentisate), the fumarate salt and/or co-crystal (e.g., a 2:1 fumarate salt and/or co-crystal, i.e., two molecules of sepiapterin to one molecule fumarate), the glycolate salt and/or co-crystal (e.g., a 3:1 glycolate salt and/or co-crystal, i.e., three molecules of sepiapterin to one molecule glycolate), the acetate salt and/or co-crystal, or the sulfate salt and/or co-crystal (e.g., a 2:1 sulfate salt and/or co-crystal, i.e., two molecules of sepiapterin to one molecule sulfate). In some embodiments, the salt and/or co-crystal is a salt with the acid. In some embodiments, the salt and/or co-crystal is a co-crystal with the acid. In some embodiments, the salt and/or co-crystal of sepiapterin have improved properties, e.g., improved stability, purity, exposure, and/or bioavailability.

In some embodiments, the salt and/or co-crystal of sepiapterin is the methanesulfonate salt and/or co-crystal.

In some embodiments, the salt and/or co-crystal of sepiapterin is the nicotinate salt and/or co-crystal.

In some embodiments, the salt and/or co-crystal of sepiapterin is the p-toluenesulfonate salt and/or co-crystal.

In some embodiments, the salt and/or co-crystal of sepiapterin is the benzenesulfonate salt and/or co-crystal.

In some embodiments, the salt and/or co-crystal of sepiapterin is the phosphate salt and/or co-crystal, wherein the phosphate counterion is $H_2PO_4^-$. In some embodiments, the salt and/or co-crystal of sepiapterin is the phosphate salt and/or co-crystal, wherein the phosphate counterion is $HPO_4^{2-}$. In some embodiments, the salt and/or co-crystal of sepiapterin is the phosphate salt and/or co-crystal, wherein the phosphate counterion is $PO_4^{3-}$. In some embodiments, the salt and/or co-crystal of sepiapterin is the 1:1 phosphate salt and/or co-crystal, i.e., one molecule of sepiapterin to one molecule phosphate. In some embodiments, the salt and/or co-crystal of sepiapterin is the 2:1 phosphate salt and/or co-crystal, i.e., two molecules of sepiapterin to one molecule phosphate.

In some embodiments, the salt and/or co-crystal of sepiapterin is the 1:1 malonate salt and/or co-crystal, i.e., one molecule of sepiapterin to one molecule malonate. In some embodiments, the salt and/or co-crystal of sepiapterin is the 2:1 malonate salt and/or co-crystal, i.e., two molecules of sepiapterin to one molecule malonate.

In some embodiments, the salt and/or co-crystal of sepiapterin is the 1:1 tartrate salt and/or co-crystal, i.e., one molecule of sepiapterin to one molecule tartrate. In some embodiments, the salt and/or co-crystal of sepiapterin is the 2:1 tartrate salt and/or co-crystal, i.e., two molecules of sepiapterin to one molecule tartrate.

In some embodiments, the salt and/or co-crystal of sepiapterin is the 1:1 gentisate salt and/or co-crystal, i.e., one molecule of sepiapterin to one molecule gentisate. In some embodiments, the salt and/or co-crystal of sepiapterin is the 2:1 gentisate salt and/or co-crystal, i.e., two molecules of sepiapterin to one molecule gentisate.

In some embodiments, the salt and/or co-crystal of sepiapterin is the 1:1 fumarate salt and/or co-crystal, i.e., one molecule of sepiapterin to one molecule fumarate. In some embodiments, the salt and/or co-crystal of sepiapterin is the 2:1 fumarate salt and/or co-crystal, i.e., two molecules of sepiapterin to one molecule fumarate.

In some embodiments, the salt and/or co-crystal of sepiapterin is the 1:1 glycolate salt and/or co-crystal, i.e., one molecule of sepiapterin to one molecule glycolate. In some embodiments, the salt and/or co-crystal of sepiapterin is the 2:1 glycolate salt and/or co-crystal, i.e., two molecules of sepiapterin to one molecule glycolate. In some embodiments, the salt and/or co-crystal of sepiapterin is the 3:1 glycolate salt and/or co-crystal, i.e., three molecules of sepiapterin to one molecule glycolate.

In some embodiments, the salt and/or co-crystal of sepiapterin is the sulfate salt and/or co-crystal, wherein the sulfate counterion is $HSO_4^-$. In some embodiments, the salt and/or co-crystal of sepiapterin is the sulfate salt and/or co-crystal, wherein the sulfate counterion is $SO_4^{2-}$. In some embodiments, the salt and/or co-crystal of sepiapterin is the 1:1 sulfate salt and/or co-crystal, i.e., one molecule of sepiapterin to one molecule sulfate. In some embodiments, the salt and/or co-crystal of sepiapterin is the 2:1 sulfate salt and/or co-crystal, i.e., two molecules of sepiapterin to one molecule sulfate.

In some embodiments, the salt and/or co-crystal of sepiapterin is the acetate salt and/or co-crystal.

In some embodiments, the pharmaceutically acceptable salt and/or co-crystal is crystalline. In some embodiments, the pharmaceutically acceptable salt and/or co-crystal includes less than 40% by weight (e.g., less than 30%, less than 20%, less than 10%, less than 5%, less than 1% or between 30-40%, 25-35%, 20-30%, 15-25%, 10-20%, 5-15%, or 1-10%) of amorphous compound. In some embodiments, the pharmaceutically acceptable salt and/or co-crystal is substantially free of amorphous compound. In some embodiments, the pharmaceutically acceptable salt and/or co-crystal is substantially free of any other salt and/or co-crystal or crystal form of sepiapterin.

In some embodiments, the pharmaceutically acceptable salt and/or co-crystal of sepiapterin is a hydrochloride salt and/or co-crystal. In some embodiments, the hydrochloride salt and/or co-crystal has an endothermic onset at about 218° C. (e.g., from 216° C. to 220° C., such as 217° C. to 219° C.) in differential scanning calorimetry (DSC) profile. In some embodiments, the hydrochloride salt and/or co-crystal has a loss of weight from 31° C. to 150° C. of less than 5%

(e.g., less than 4%, less than 3%, less than 2%, or less than 1%) as measured by thermal gravimetric analysis.

In some embodiments, the hydrochloride salt and/or co-crystal has at least one peak at diffraction angle 2θ (°) of 7.8±0.5 as measured by X-ray powder diffractometry. In some embodiments, the hydrochloride salt and/or co-crystal further has at least one peak at diffraction angle 2θ (°) of 7.8±0.5, 12.9±0.5, and/or 26.2±0.5 as measured by X-ray powder diffractometry. In some embodiments, the hydrochloride salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 6 as measured by X-ray powder diffractometry. In some embodiments, the hydrochloride salt and/or co-crystal has all of the peaks listed in Table 6 as measured by X-ray powder diffractometry.

TABLE 6

XRPD peak list for the hydrochloride salt and/or co-crystal of sepiapterin

| 2θ (°) | Intensity |
|---|---|
| 7.8 | 100.00 |
| 8.9 | 6.89 |
| 12.9 | 58.56 |
| 15.6 | 8.52 |
| 17.9 | 25.23 |
| 19.2 | 5.48 |
| 21.1 | 10.97 |
| 23.6 | 25.15 |
| 25.2 | 22.66 |
| 26.2 | 45.91 |
| 27.6 | 32.94 |
| 30.3 | 10.50 |
| 31.7 | 7.83 |
| 34.2 | 8.87 |
| 36.7 | 3.67 |

In some embodiments, the pharmaceutically acceptable salt and/or co-crystal of sepiapterin is a methanesulfonate salt and/or co-crystal. In some embodiments, the methanesulfonate salt and/or co-crystal has an endothermic onset at about 182° C. (e.g., from 180° C. to 184° C., such as 181° C. to 183° C.) in differential scanning calorimetry (DSC) profile. In some embodiments, the methanesulfonate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the methanesulfonate salt and/or co-crystal has at least one peak at diffraction angle 2θ (°) of 23.5±0.5 as measured by X-ray powder diffractometry. In some embodiments, the methanesulfonate salt and/or co-crystal further has at least one peak at diffraction angle 2θ (°) of 7.9±0.5, 23.5±0.5, and/or 29.0±0.5 as measured by X-ray powder diffractometry. In some embodiments, the methanesulfonate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 7 as measured by X-ray powder diffractometry. In some embodiments, the methanesulfonate salt and/or co-crystal has all of the peaks listed in Table 7 as measured by X-ray powder diffractometry.

TABLE 7

XRPD peak list for the methanesulfonate salt and/or co-crystal Form 1 of sepiapterin

| 2θ (°) | Intensity |
|---|---|
| 7.9 | 21.77 |
| 11.7 | 8.20 |
| 13.7 | 8.52 |
| 15.7 | 4.79 |
| 16.6 | 5.34 |
| 18.0 | 5.66 |
| 19.8 | 2.10 |
| 20.3 | 5.36 |
| 20.9 | 2.43 |
| 22.3 | 4.25 |
| 22.7 | 2.15 |
| 23.5 | 100.00 |
| 24.7 | 3.69 |
| 25.6 | 2.70 |
| 26.8 | 1.79 |
| 27.2 | 1.68 |
| 28.3 | 2.75 |
| 29.0 | 57.60 |
| 29.8 | 5.18 |
| 30.5 | 1.37 |
| 32.2 | 4.66 |
| 33.0 | 1.64 |
| 36.5 | 1.29 |

In some embodiments, the methanesulfonate salt and/or co-crystal has at least one peak at diffraction angle 2θ (°) of 7.9±0.5 as measured by X-ray powder diffractometry. In some embodiments, the methanesulfonate salt and/or co-crystal further has at least one peak at diffraction angle 2θ (°) of 7.9±0.5, 23.4±0.5, and/or 28.9±0.5 as measured by X-ray powder diffractometry. In some embodiments, the methanesulfonate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 8 as measured by X-ray powder diffractometry. In some embodiments, the methanesulfonate salt and/or co-crystal has all of the peaks listed in Table 8 as measured by X-ray powder diffractometry.

TABLE 8

XRPD peak list for the methanesulfonate salt and/or co-crystal Form 2 of sepiapterin

| 2θ (°) | Intensity |
|---|---|
| 7.9 | 100.00 |
| 11.0 | 21.32 |
| 12.1 | 22.02 |
| 13.5 | 79.87 |
| 15.7 | 11.87 |
| 17.8 | 9.81 |
| 19.7 | 10.93 |
| 21.3 | 26.79 |
| 23.4 | 96.13 |
| 24.1 | 24.88 |
| 24.3 | 22.10 |
| 25.5 | 9.45 |
| 26.0 | 11.27 |
| 27.6 | 7.63 |
| 28.9 | 95.64 |
| 31.2 | 4.39 |
| 36.1 | 6.65 |

In some embodiments, the pharmaceutically acceptable salt and/or co-crystal of sepiapterin is a nicotinate salt and/or co-crystal. In some embodiments, the nicotinate salt and/or co-crystal has an endothermic onset at about 220° C. (e.g., from 218° C. to 222° C., such as 219° C. to 221° C.) in differential scanning calorimetry (DSC) profile. In some embodiments, the nicotinate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the nicotinate salt and/or co-crystal has at least one peak at diffraction angle 2θ (°) of 24.5±0.5 as measured by X-ray powder diffractometry. In some embodiments, the nicotinate salt and/or co-crystal further has at least one peak at diffraction angle 2θ (°) of 9.9±0.5, 23.2±0.5, and/or 24.5±0.5 as measured by X-ray powder diffractometry. In some embodiments, the nicotinate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 9 as measured by X-ray powder diffractometry. In some embodiments, the nicotinate salt and/or co-crystal has all of the peaks listed in Table 9 as measured by X-ray powder diffractometry.

TABLE 9

XRPD peak list for the nicotinate salt and/or co-crystal of sepiapterin

| 2θ (°) | Intensity |
|---|---|
| 9.5 | 10.29 |
| 9.9 | 53.95 |
| 11.5 | 9.31 |
| 12.0 | 11.76 |
| 14.7 | 14.20 |
| 15.9 | 17.61 |
| 17.5 | 7.53 |
| 19.0 | 5.37 |
| 20.8 | 5.88 |
| 21.3 | 6.12 |
| 21.7 | 7.20 |
| 23.2 | 34.05 |
| 24.5 | 100.00 |
| 25.2 | 12.90 |
| 28.0 | 8.51 |
| 31.1 | 5.39 |
| 32.3 | 4.52 |
| 33.4 | 8.02 |
| 35.1 | 5.05 |

In some embodiments, the salt and/or co-crystal of sepiapterin is a toluenesulfonate salt and/or co-crystal. In some embodiments, the toluenesulfonate salt and/or co-crystal has an endothermic onset at about 190° C. (e.g., from 188° C. to 192° C., such as 189° C. to 191° C.) and/or 263° C. (e.g., from 261° C. to 265° C., 262° C. to 264° C.) in differential scanning calorimetry (DSC) profile. In some embodiments, the toluenesulfonate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the toluenesulfonate salt and/or co-crystal has at least one peak at diffraction angle 2θ (°) of 6.5±0.5 as measured by X-ray powder diffractometry. In some embodiments, the toluenesulfonate salt and/or co-crystal further has at least one peak at diffraction angle 2θ (°) of 6.5±0.5, 15.1±0.5, and/or 23.4±0.5 as measured by X-ray powder diffractometry. In some embodiments, the toluenesulfonate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 10 as measured by X-ray powder diffractometry. In some embodiments, the toluenesulfonate salt and/or co-crystal has all of the peaks listed in Table 10 as measured by X-ray powder diffractometry.

TABLE 10

XRPD peak list for the toluenesulfonate salt and/or co-crystal of sepiapterin

| 2θ (°) | Intensity |
|---|---|
| 6.5 | 100.00 |
| 12.9 | 1.79 |
| 14.3 | 1.39 |
| 15.1 | 15.36 |
| 16.2 | 5.33 |
| 18.4 | 8.96 |
| 19.6 | 3.06 |
| 20.2 | 4.86 |
| 21.8 | 2.23 |
| 22.5 | 2.95 |
| 23.1 | 7.99 |
| 23.4 | 9.14 |
| 24.5 | 1.81 |
| 26.0 | 2.48 |
| 27.0 | 4.49 |
| 27.3 | 3.93 |
| 28.1 | 5.31 |
| 28.4 | 5.59 |
| 28.8 | 2.05 |
| 30.6 | 2.24 |
| 31.0 | 1.98 |
| 32.6 | 1.82 |

In some embodiments, the salt and/or co-crystal of sepiapterin is a benzenesulfonate salt and/or co-crystal. In some embodiments, the benzenesulfonate salt and/or co-crystal has an endothermic onset at about 193° C. (e.g., from 191° C. to 195° C., such as 192° C. to 194° C.) and/or 206° C. (e.g., from 204° C. to 208° C., 205° C. to 207° C.) in differential scanning calorimetry (DSC) profile. In some embodiments, the benzenesulfonate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the benzenesulfonate salt and/or co-crystal has at least one peak at diffraction angle 2θ (°) of 6.5±0.5 as measured by X-ray powder diffractometry. In some embodiments, the benzenesulfonate salt and/or co-crystal further has at least one peak at diffraction angle 2θ (°) of 6.5±0.5, 14.8±0.5, and/or 19.6±0.5 as measured by X-ray powder diffractometry. In some embodiments, the benzenesulfonate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 11 as measured by X-ray powder diffractometry. In some embodiments, the benzenesulfonate salt and/or co-crystal has all of the peaks listed in Table 11 as measured by X-ray powder diffractometry.

TABLE 11

XRPD peak list for the benzenesulfonate salt and/or co-crystal of sepiapterin

| 2θ (°) | Intensity |
|---|---|
| 4.9 | 5.90 |
| 6.5 | 100.00 |
| 14.8 | 16.73 |
| 17.8 | 4.23 |

TABLE 11-continued

XRPD peak list for the benzenesulfonate salt and/or co-crystal of sepiapterin

| 2θ (°) | Intensity |
|---|---|
| 19.6 | 7.98 |
| 21.5 | 2.49 |
| 23.7 | 3.46 |
| 24.5 | 3.84 |
| 26.1 | 3.29 |

In some embodiments, the salt and/or co-crystal of sepiapterin is a sulfate salt. In some embodiments, the sulfate salt and/or co-crystal has an endothermic onset at about 196° C. (e.g., from 194° C. to 198° C., such as 195° C. to 197° C.) in differential scanning calorimetry (DSC) profile. In some embodiments, the sulfate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the sulfate salt and/or co-crystal has at least one peak at diffraction angle 2θ (°) of 5.1±0.5 as measured by X-ray powder diffractometry. In some embodiments, the sulfate salt and/or co-crystal further has at least one peak at diffraction angle 2θ (°) of 5.1±0.5, 7.8±0.5, and/or 23.0±0.5 as measured by X-ray powder diffractometry. In some embodiments, the sulfate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 12 as measured by X-ray powder diffractometry. In some embodiments, the sulfate salt and/or co-crystal has all of the peaks listed in Table 12 as measured by X-ray powder diffractometry.

TABLE 12

XRPD peak list for the sulfate salt and/or co-crystal of sepiapterin

| 2θ (°) | Intensity |
|---|---|
| 5.1 | 100.00 |
| 6.8 | 3.33 |
| 7.8 | 43.48 |
| 10.2 | 15.92 |
| 15.7 | 18.13 |
| 17.2 | 8.33 |
| 18.7 | 6.49 |
| 19.8 | 5.19 |
| 21.3 | 5.52 |
| 23.0 | 19.05 |
| 23.5 | 8.29 |
| 24.2 | 5.59 |
| 24.8 | 17.44 |
| 25.7 | 4.97 |
| 26.7 | 10.38 |
| 28.7 | 11.49 |
| 30.4 | 2.88 |
| 31.0 | 3.67 |

In some embodiments, the pharmaceutically acceptable salt and/or co-crystal of sepiapterin is a phosphate salt and/or co-crystal. In some embodiments, the phosphate salt and/or co-crystal has an endothermic onset at about 144° C. (e.g., from 142° C. to 146° C., such as 143° C. to 145° C.) and/or 207° C. (e.g., from 205° C. to 209° C., 206° C. to 208° C.) in differential scanning calorimetry (DSC) profile. In some embodiments, the phosphate salt and/or co-crystal has a loss of weight from 31° C. to 150° C. of less than 12% (e.g., less than 10%, less than 5%, less than 2%, or less than 1%) as measured by thermal gravimetric analysis.

In some embodiments, the phosphate salt and/or co-crystal has at least one peak at diffraction angle 2θ (°) of 25.6±0.5 as measured by X-ray powder diffractometry. In some embodiments, the phosphate salt and/or co-crystal further has at least one peak at diffraction angle 2θ (°) of 16.6±0.5, 22.2±0.5, and/or 25.6±0.5 as measured by X-ray powder diffractometry. In some embodiments, the phosphate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 13 as measured by X-ray powder diffractometry. In some embodiments, the phosphate salt and/or co-crystal has all of the peaks listed in Table 13 as measured by X-ray powder diffractometry.

TABLE 13

XRPD peak list for the phosphate salt and/or co-crystal of sepiapterin

| 2θ (°) | Intensity |
|---|---|
| 5.5 | 4.41 |
| 8.1 | 1.21 |
| 8.9 | 2.21 |
| 10.3 | 1.79 |
| 10.8 | 5.80 |
| 15.3 | 1.84 |
| 16.6 | 8.35 |
| 17.7 | 1.95 |
| 20.3 | 1.40 |
| 21.2 | 1.61 |
| 22.2 | 9.77 |
| 23.1 | 1.74 |
| 25.6 | 100.00 |
| 30.8 | 6.31 |
| 31.1 | 4.85 |
| 33.5 | 0.73 |
| 36.0 | 1.70 |

In some embodiments, the salt and/or co-crystal of sepiapterin is a malonate salt and/or co-crystal. In some embodiments, the malonate salt and/or co-crystal has an endothermic onset at about 175° C. (e.g., from 173° C. to 177° C., such as 174° C. to 176° C.) in differential scanning calorimetry (DSC) profile. In some embodiments, the malonate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the malonate salt and/or co-crystal has at least one peak at diffraction angle 2θ (°) of 6.9±0.5 as measured by X-ray powder diffractometry. In some embodiments, the malonate salt and/or co-crystal further has at least one peak at diffraction angle 2θ (°) of 6.9±0.5, 23.8±0.5, and/or 25.5±0.5 as measured by X-ray powder diffractometry. In some embodiments, the malonate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 14 as measured by X-ray powder diffractometry. In some embodiments, the malonate salt and/or co-crystal has all of the peaks listed in Table 14 as measured by X-ray powder diffractometry.

TABLE 14

XRPD peak list for the malonate
salt and/or co-crystal of sepiapterin

| 2θ (°) | Intensity |
| --- | --- |
| 6.9 | 100.00 |
| 8.4 | 13.11 |
| 10.6 | 7.62 |
| 16.4 | 5.63 |
| 17.8 | 9.73 |
| 19.3 | 8.96 |
| 20.1 | 9.99 |
| 22.2 | 10.50 |
| 22.7 | 20.52 |
| 23.8 | 34.02 |
| 24.5 | 5.82 |
| 25.5 | 24.50 |
| 26.6 | 4.00 |
| 27.3 | 6.96 |
| 29.8 | 5.38 |
| 33.1 | 12.08 |

In some embodiments, the salt and/or co-crystal of sepiapterin is a tartrate salt and/or co-crystal (e.g., an L-tartrate salt and/or co-crystal). In some embodiments, the tartrate salt and/or co-crystal has an endothermic onset at about 156° C. (e.g., from 154° C. to 158° C., such as 155° C. to 157° C.) and/or 175° C. (e.g., from 173° C. to 177° C., such as 174° C. to 176° C.) in differential scanning calorimetry (DSC) profile. In some embodiments, the tartrate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the tartrate salt and/or co-crystal has at least one peak at diffraction angle 2θ (°) of 7.4±0.5 as measured by X-ray powder diffractometry. In some embodiments, the tartrate salt and/or co-crystal further has at least one peak at diffraction angle 2θ (°) of 7.4±0.5, 21.8±0.5, and/or 23.9±0.5 as measured by X-ray powder diffractometry. In some embodiments, the tartrate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 15 as measured by X-ray powder diffractometry. In some embodiments, the tartrate salt and/or co-crystal has all of the peaks listed in Table 15 as measured by X-ray powder diffractometry.

TABLE 15

XRPD peak list for the L-tartrate
salt and/or co-crystal of sepiapterin

| 2θ (°) | Intensity |
| --- | --- |
| 7.4 | 100.00 |
| 10.1 | 47.99 |
| 14.2 | 82.76 |
| 14.7 | 27.06 |
| 19.1 | 21.16 |
| 20.2 | 29.91 |
| 21.8 | 85.30 |
| 22.1 | 53.68 |
| 23.9 | 85.30 |
| 24.9 | 19.26 |
| 25.5 | 28.45 |
| 26.8 | 18.58 |
| 29.7 | 21.59 |
| 31.6 | 10.10 |
| 32.9 | 22.18 |

In some embodiments, the salt and/or co-crystal of sepiapterin is a fumarate salt and/or co-crystal. In some embodiments, the fumarate salt and/or co-crystal has an endothermic onset at about 77° C. (e.g., from 75° C. to 79° C., such as 76° C. to 78° C.), 133° C. (e.g., from 131° C. to 135° C., such as 132° C. to 134° C.), and/or 190° C. (e.g., from 188° C. to 192° C., such as 189° C. to 191° C.) in differential scanning calorimetry (DSC) profile. In some embodiments, the fumarate salt and/or co-crystal has a loss of weight from 31° C. to 150° C. of less than 5% (e.g., less than 4%, less than 3%, less than 2%, or less than 1%) as measured by thermal gravimetric analysis.

In some embodiments, the fumarate salt and/or co-crystal has at least one peak at diffraction angle 2θ (°) of 24.0±0.5 as measured by X-ray powder diffractometry. In some embodiments, the fumarate salt and/or co-crystal further has at least one peak at diffraction angle 2θ (°) of 11.4±0.5, 11.9±0.5, and/or 24.0±0.5 as measured by X-ray powder diffractometry. In some embodiments, the fumarate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 16 as measured by X-ray powder diffractometry. In some embodiments, the fumarate salt and/or co-crystal has all of the peaks listed in Table 16 as measured by X-ray powder diffractometry.

TABLE 16

XRPD peak list for the fumarate
salt and/or co-crystal of sepiapterin

| 2θ (°) | Intensity |
| --- | --- |
| 6.1 | 6.43 |
| 7.7 | 5.40 |
| 11.4 | 53.62 |
| 11.9 | 33.37 |
| 14.2 | 8.03 |
| 16.5 | 6.70 |
| 18.3 | 13.86 |
| 19.0 | 6.68 |
| 20.7 | 10.02 |
| 21.3 | 7.02 |
| 22.8 | 24.68 |
| 24.0 | 100.00 |
| 28.3 | 33.26 |
| 32.7 | 6.35 |
| 36.0 | 3.28 |
| 38.5 | 6.02 |

In some embodiments, the salt of sepiapterin is a gentisate salt and/or co-crystal. In some embodiments, the gentisate salt and/or co-crystal has an endothermic onset at about 83° C. (e.g., from 81° C. to 85° C., such as 82° C. to 84° C.), 134° C. (e.g., from 132° C. to 136° C., such as 133° C. to 135° C.), and/or 149° C. (e.g., from 147° C. to 151° C., such as 148° C. to 150° C.) in differential scanning calorimetry (DSC) profile. In some embodiments, the gentisate salt and/or co-crystal has a loss of weight from 31° C. to 150° C. of less than 7% (e.g., less than 5%, less than 3%, less than 2%, or less than 1%) as measured by thermal gravimetric analysis.

In some embodiments, the gentisate salt and/or co-crystal has at least one peak at diffraction angle 2θ (°) of 7.1±0.5 as measured by X-ray powder diffractometry. In some embodiments, the gentisate salt and/or co-crystal further has at least one peak at diffraction angle 2θ (°) of 7.1±0.5, 8.7±0.5, and/or 26.7±0.5 as measured by X-ray powder diffractometry. In some embodiments, the gentisate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 17 as measured by X-ray powder diffractometry. In some embodiments, the gentisate salt and/or co-crystal has all of the peaks listed in Table 17 as measured by X-ray powder diffractometry.

TABLE 17

XRPD peak list for the gentisate salt and/or co-crystal of sepiapterin

| 2θ (°) | Intensity |
| --- | --- |
| 5.7 | 17.29 |
| 7.1 | 100.00 |
| 8.7 | 42.69 |
| 10.4 | 3.94 |
| 11.3 | 11.69 |
| 12.1 | 4.13 |
| 14.3 | 21.10 |
| 16.0 | 6.46 |
| 16.4 | 5.94 |
| 17.0 | 5.85 |
| 17.6 | 7.93 |
| 19.1 | 8.27 |
| 20.20 | 3.47 |
| 20.7 | 2.90 |
| 21.5 | 3.37 |
| 23.6 | 2.69 |
| 24.4 | 4.50 |
| 26.7 | 52.20 |
| 27.1 | 35.49 |
| 28.2 | 8.74 |
| 28.9 | 4.31 |
| 29.9 | 2.62 |
| 31.4 | 2.99 |
| 34.4 | 1.28 |
| 35.8 | 3.54 |
| 37.6 | 0.57 |

In some embodiments, the salt of sepiapterin is a glycolate salt and/or co-crystal. In some embodiments, the glycolate salt and/or co-crystal has an endothermic onset at about 79° C. (e.g., from 77° C. to 81° C., such as 78° C. to 80° C.), 90° C. (e.g., from 88° C. to 92° C., such as 89° C. to 91° C.), 132° C. (e.g., from 130° C. to 134° C., such as 131° C. to 133° C.), and/or 152° C. (e.g., from 150° C. to 154° C., such as 151° C. to 153° C.) in differential scanning calorimetry (DSC) profile. In some embodiments, the glycolate salt and/or co-crystal has a loss of weight from 31° C. to 150° C. of less than 21% (e.g., less than 15%, less than 10%, less than 5%, or less than 1%) as measured by thermal gravimetric analysis.

In some embodiments, the glycolate salt and/or co-crystal has at least one peak at diffraction angle 2θ (°) of 7.6±0.5 as measured by X-ray powder diffractometry. In some embodiments, the glycolate salt and/or co-crystal further has at least one peak at diffraction angle 2θ (°) of 7.6±0.5, 10.7±0.5, and/or 24.0±0.5 as measured by X-ray powder diffractometry. In some embodiments, the glycolate salt and/or co-crystal has one or more (e.g., two or more, three or more, four or more, five or more, six or more, seven or more, eight or more, nine or more, ten or more, eleven or more, twelve or more, thirteen or more, or fourteen or more) peaks listed in Table 18 as measured by X-ray powder diffractometry. In some embodiments, the glycolate salt and/or co-crystal has all of the peaks listed in Table 18 as measured by X-ray powder diffractometry.

TABLE 18

XRPD peak list for the glycolate salt and/or co-crystal of sepiapterin

| 2θ (°) | Intensity |
| --- | --- |
| 4.8 | 6.23 |
| 7.6 | 100.00 |
| 10.3 | 68.06 |
| 10.7 | 70.69 |
| 15.3 | 36.51 |
| 18.2 | 24.25 |
| 18.7 | 27.26 |
| 19.9 | 2.66 |
| 21.2 | 17.11 |
| 24.0 | 96.62 |
| 24.4 | 18.44 |
| 28.8 | 47.57 |
| 30.3 | 7.43 |
| 32.5 | 4.42 |
| 33.3 | 7.49 |
| 34.3 | 5.21 |
| 36.3 | 7.37 |

In some embodiments of any of the foregoing compositions, the sepiapterin or salt and/or co-crystal thereof is formulated in particles less than 200 μm (e.g., less than 180 μm, less than 160 μm, less than 140 μm, less than 120 μm, less than 100 μm, or less than 80 μm) in size.

In some embodiments of any of the foregoing compositions, the pharmaceutical composition is formulated as particles (e.g., particles for use in a suspension). In some embodiments, the particles are less than 200 μm (e.g., less than 180 μm, less than 160 μm, less than 140 μm, less than 120 μm, less than 100 μm, or less than 80 μm) in size.

In some embodiments of any of the foregoing compositions, the pharmaceutical composition includes less than 50% (e.g., less than 40%, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, or less than 0.2%) of lactoylpterin by weight of the combined amount of sepiapterin, or salt and/or co-crystal thereof, and lactoylpterin in the composition. In some embodiments, the pharmaceutical composition includes less than 1.3% lactoylpterin.

In some embodiments of any of the foregoing compositions, the pharmaceutical composition further includes a dosing vehicle (e.g., dosing vehicle with a viscosity of about 50-1750 centipoise).

In some embodiments of any of the foregoing compositions, the pharmaceutical composition upon administration to a subject, results in greater plasma or liver cell levels (e.g., at least 1.1 times, at least 1.2 times, at least 1.3 times, at least 1.4 times, at least 1.5 times, at least 2 times, at least 3 times, or at least 4 times) of tetrahydrobiopterin (e.g., as measured by Tmax, Cmax, AUC, or concentration in the plasma at 15 minutes after administration) compared to that resulting from administration of a pharmaceutical composition including an equivalent dose of tetrahydrobiopterin.

In some embodiments of any of the foregoing compositions, the pharmaceutical composition, upon administration to a subject, results greater plasma or liver cell levels (e.g., at least 1.1 times, at least 1.2 times, at least 1.3 times, at least 1.4 times, at least 1.5 times, at least 2 times, at least 3 times, or at least 4 times) of tetrahydrobiopterin (e.g., as measured by Tmax, Cmax, AUC, or concentration in the plasma at 15 minutes after administration) compared to that resulting from administration of a pharmaceutical composition including an equivalent dose of sepiapterin, or a pharmaceutically acceptable salt and/or co-crystal thereof, and more than 10% antioxidant.

In an aspect, the invention features a method of producing a pharmaceutical composition including sepiapterin, or a pharmaceutically acceptable salt and/or co-crystal thereof. This method includes: a) mixing microcrystalline cellulose and/or colloidal silicon dioxide; b) adding sepiapterin, or a pharmaceutically acceptable salt and/or co-crystal thereof, a dispersant, and/or an antioxidant to the mixture of step a; and c) mixing the microcrystalline cellulose, colloidal silicon dioxide, sepiapterin, or a pharmaceutically acceptable salt and/or co-crystal thereof, dispersant, and/or antioxidant, thereby producing a pharmaceutical composition including sepiapterin, or a pharmaceutically acceptable salt and/or co-crystal thereof. In some embodiments, step a), b) and c) may be done in any order.

In some embodiments, the mixture of microcrystalline cellulose and colloidal silicon dioxide is passed through a filter with pores of less than 200 μm (e.g., less than 180 μm, less than 160 μm, less than 140 μm, less than 120 μm, less than 100 μm, or less than 80 μm) prior to step b.

In some embodiments, the mixture of microcrystalline cellulose, colloidal silicon dioxide, sepiapterin, or a pharmaceutically acceptable salt and/or co-crystal thereof, dispersant, and antioxidant is passed through a filter with pores of less than 200 μm (e.g., less than 180 μm, less than 160 μm, less than 140 μm, less than 120 μm, less than 100 μm, or less than 80 μm).

In some embodiments of any of the foregoing compositions, the percentages by weight are measured for the dry composition (e.g., prior to suspension in a liquid such as water). In some embodiments, when sepiapterin, or a pharmaceutically acceptable salt and/or co-crystal thereof, is present in the composition as a pharmaceutically acceptable salt and/or co-crystal, the weight is the weight of sepiapterin, or a pharmaceutically acceptable salt and/or co-crystal thereof, not including the counterion.

In some embodiments of any of the foregoing methods, the antioxidant is ascorbic acid. In some embodiments of any of the foregoing methods, the dispersant is croscarmellose sodium.

In an aspect, the invention features a method for treating a tetrahydrobiopterin-related disorder (e.g., phenylketonuria or a tetrahydrobiopterin deficiency) in a subject in need thereof, the method including administering an effective amount of any of the foregoing pharmaceutical compositions.

In an aspect, the invention features a method of increasing tetrahydrobiopterin levels in a subject in need thereof, the method including administering to the subject an effective amount of any of the foregoing pharmaceutical compositions.

In an aspect, the invention features a method of decreasing phenylalanine levels in a subject in need thereof, the method including administering to the subject an effective amount of any of the foregoing pharmaceutical compositions.

In an aspect, the invention features, a method of increasing the activity of phenylalanine hydroxylase in a subject, the method including administering to the subject an effective amount of any of the foregoing pharmaceutical compositions.

In an aspect, the invention features a method of treating phenylketonuria in a subject in need thereof, the method including administering to the subject an effective amount of any of the foregoing pharmaceutical compositions.

In an aspect, the invention features a method of treating gastroparesis in a subject in need thereof, the method including administering to the subject an effective amount of any of the foregoing pharmaceutical compositions.

In an aspect, the invention features a method of increasing serotonin levels in a subject in need thereof, the method including administering to the subject an effective amount of any of the foregoing pharmaceutical compositions.

In an aspect, the invention features a method of increasing the activity of tryptophan hydroxylase in a subject, the method including administering to the subject an effective amount of any of the foregoing pharmaceutical compositions.

In an aspect, the invention features a method of increasing dopamine levels in a subject in need thereof, the method including administering to the subject an effective amount of any of the foregoing pharmaceutical compositions.

In an aspect, the invention features a method of increasing the activity of tyrosine hydroxylase in a subject, the method including administering to the subject an effective amount of any of the foregoing pharmaceutical compositions.

In an aspect, the invention features a method of increasing the activity of nitric oxide synthases in a subject, the method including administering to the subject an effective amount of any of the foregoing pharmaceutical compositions.

In an aspect, the invention features a method of increasing the activity of alkylglycerol monooxygenase in a subject, the method including administering to the subject an effective amount of any of the foregoing pharmaceutical compositions.

In some embodiments of any of the foregoing methods, the effective amount of any of the foregoing pharmaceutical compositions includes an amount sufficient to increase the level of tetrahydrobiopterin in the plasma of the subject 1 hour after administration by at least a factor of two (e.g., at least a factor of 3, 4, 5, 6, 7, 9, or 10) compared to the level of tetrahydrobiopterin prior to administration.

In some embodiments of any of the foregoing methods, the effective amount of any of the foregoing pharmaceutical compositions includes an amount sufficient to increase the level of tetrahydrobiopterin in the CSF and/or brain of the subject 1 hour after administration by at least a factor of two (e.g., at least a factor of 3, 4, 5, 6, 7, 9, or 10) compared to the level of tetrahydrobiopterin prior to administration.

In some embodiments of any of the foregoing methods, the subject is human. In some embodiments of any of the foregoing methods, the method includes combining any of the foregoing pharmaceutical compositions with a dosing vehicle prior to administration.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

As used herein, the term "administration" refers to the administration of a composition to a subject. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal, or vitreal.

The term "anti-caking agent" refers to an additive added to powdered or granulated pharmaceutical formulations to prevent the formation of lumps. Exemplary anti-caking agents include colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, and polydimethylsiloxane.

The term "antioxidant" refers to agents that can minimize the oxidative degradation of an active pharmaceutical ingredient. Examples of antioxidants include ascorbic acid, tocopherol, retinol, ascorbyl palmitate, N-acetyl cysteine, glutathione, ethylenediaminetetraacetic acid, sodium bisulfite, sodium metabisulfite, thiourea, butylatedhydroxytoluene, butylatedhydroxyanisole, vitamin E, 4-chloro-2,6-di-tert-butylphenol, alkylated diphenylamines, ascorbyl myristate, ascorbyl stearate, beta-carotene, citric acid, cysteine, D-alpha-tocopheryl polyethylene glycol 1000 succinate, deferoxamine methanesulfonate, dodecyl gallate, ethylparaben, folic acid, fumaric acid, gallic acid, lecithin, malic acid, methylparaben, monothioglycerol, nordihydroguaiaretic acid, octyl gallate, p-phenylenediamine, potassium ascorbate, potassium metabisulfite, potassium sorbate, propionic acid, propyl gallate, sorbic acid, sodium ascorbate, sodium hydrosulfite, sodium isoascorbate, sodium sulfite, sodium thiosulfate, tartaric acid, tert-butylhydroquinone, tocopheryl acetate, vitamin A, vitamin B6, and vitamin B12.

As used herein, the term "BH4-related disorder" or "tetrahydrobiopterin-related disorder," refers to any disease or disorder that may derive a therapeutic benefit from modulation (e.g., increase) of the level of BH4, e.g., phenylketonuria.

By "determining the level of a compound" is meant the detection of a compound, by methods known in the art either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value).

Methods to measure compound levels generally include, but are not limited to, liquid chromatography (LC)-mass spectrometry.

The term "dispersant" refers to an agent used in pharmaceutical formulations, which causes particles in a formulation to separate, e.g., release their medicinal substances on contact with moisture. Examples include crosslinked polyvinylpyrrolidone, carboxymethylcellulose (e.g., croscarmellose salt, e.g., croscarmellose sodium), starch (e.g., sodium starch glycolate), or alginic acid.

An "effective amount" of a compound may vary according to factors such as the disease state, age, sex, and weight of the individual, and the ability of the compound to elicit the desired response. A therapeutically effective amount encompasses an amount in which any toxic or detrimental effects of the compound are outweighed by the therapeutically beneficial effects. A therapeutically effective amount also encompasses an amount sufficient to confer benefit, e.g., clinical benefit.

By "increasing the activity of" an enzyme, is meant increasing the level of an activity related to the enzyme, e.g., phenylalanine hydroxylase, or a related downstream effect. A non-limiting example of increasing an activity of an enzyme includes increasing the activity of phenylalanine hydroxylase resulting in a decrease in the level of phenylalanine. The activity level of an enzyme may be measured using any method known in the art.

By "level" is meant a level of a compound, as compared to a reference. The reference can be any useful reference, as defined herein. By a "decreased level" or an "increased level" of a compound is meant a decrease or increase in compound level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a compound may be expressed in mass/vol (e.g., g/dL, mg/mL, µg/mL, ng/mL) or percentage relative to total compound in a sample.

The term "pharmaceutical composition," as used herein, represents a composition containing a compound described herein formulated with a pharmaceutically acceptable excipient. A pharmaceutical composition may be one manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gel cap, suspension, solution, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

As used herein, the term "pharmaceutically acceptable salt" means any pharmaceutically acceptable salt of sepiapterin. Pharmaceutically acceptable salts include ion pairs of sepiapterin in the solid state and/or in solution. A pharmaceutically acceptable co-crystal includes freebase sepiapterin and an acid in a solid state. Mixture of the salt form and co-crystal form may be present in the same composition. For example, pharmaceutically acceptable salts of sepiapterin include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: in Remington (Remington: The Science and Practice of Pharmacy, (22nd ed.) ed. L. V. Allen, Jr., 2013, Pharmaceutical Press, Philadelphia, Pa.). The salts can be prepared in situ during the final isolation and purification of the compounds described herein or separately by reacting a free base group with a suitable organic acid. Sepiapterin may be prepared as pharmaceutically acceptable salts and/or co-crystals. These salts may be acid addition salts involving inorganic or organic acids. Suitable pharmaceutically acceptable acids and methods for preparation of the appropriate salts are well-known in the art.

Representative acid addition salts include 4-acetamidobenzoate, acetate, adipate, alginate, 4-aminosalicylate, ascorbate, aspartate, benzenesulfonate, benzoate, bisulfate, borate, butyrate, camphorate, camphorsulfonate, carbonate, cinnimate, citrate, cyclopentanepropionate, cyclamate, decanoate, 2,2,-dichloroacetate, digluconate, dodecylsulfate, ethane-1,2-disulfonate, ethanesulfonate, formate, fumarate, galactarate, gentisate, glucoheptonate, gluconate, glucoronate, glutamate, glutarate, glycerophosphate, glycolate, hemisulfate, heptonate, hexanoate, hippurate, hydrobromide, hydrochloride, hydroiodide, 1-hydroxy-2-naphthoate, 2-hydroxy-ethanesulfonate, isobutyrate, lactobionate, lactate, laurate, lauryl sulfate, malate, maleate, malonate, mandolate, methanesulfonate, naphthalene-1,5-disulfonate, 2-naphthalenesulfonate, nicotinate, nitrate, octanoate, oleate, oxalate, 2-oxoglutarate, palmitate, pamoate, pectinate, persulfate, 3-phenylpropionate, phosphate, picrate, pivalate, propionate, pyroglutamate, salicylate, sebacate, stearate, succinate, sulfate, tartrate, thiocyanate, toluenesulfonate, undecanoate, and valerate salts.

By a "reference" is meant any useful reference used to compare compound levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified compound (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound of the invention. In preferred embodiments, the reference sample, standard, or level is matched to the sample subject sample by at least one of the following criteria: age, weight, sex, disease stage, and overall health. A standard curve of levels of a purified compound, e.g., any described herein, within the normal reference range can also be used as a reference.

As used herein, the term "subject" or "patient" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

BRIEF DESCRIPTION OF THE FIGURES

FIG. 1 is a table illustrating the protocol for pharmacokinetic studies of pharmaceutical compositions of the invention.

FIG. 3 is a table illustrating tetrahydrobiopterin levels in the kidney, liver, and urine upon treatment with tetrahydrobiopterin or sepiapterin.

DETAILED DESCRIPTION

Figure 2:
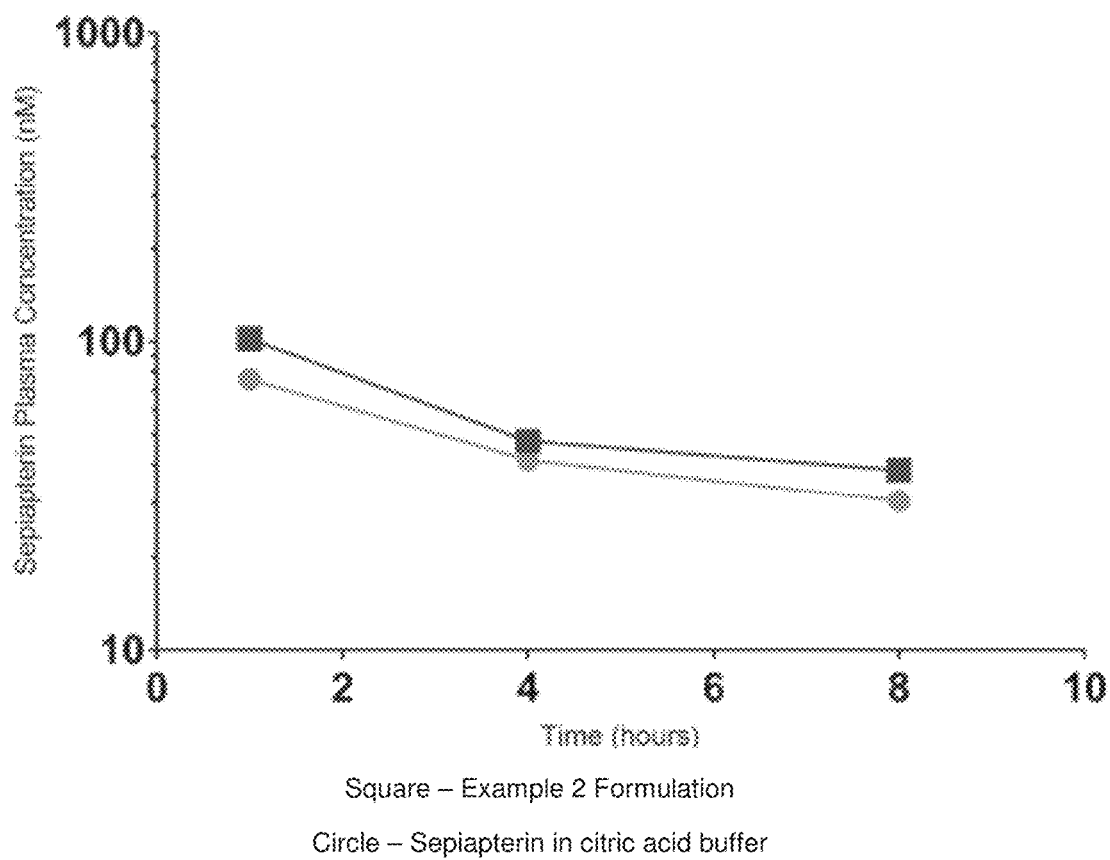
FIG. 2 is a graph illustrating plasma concentration of sepiapterin after administration of pharmaceutical compositions of the invention.
Figure 4:
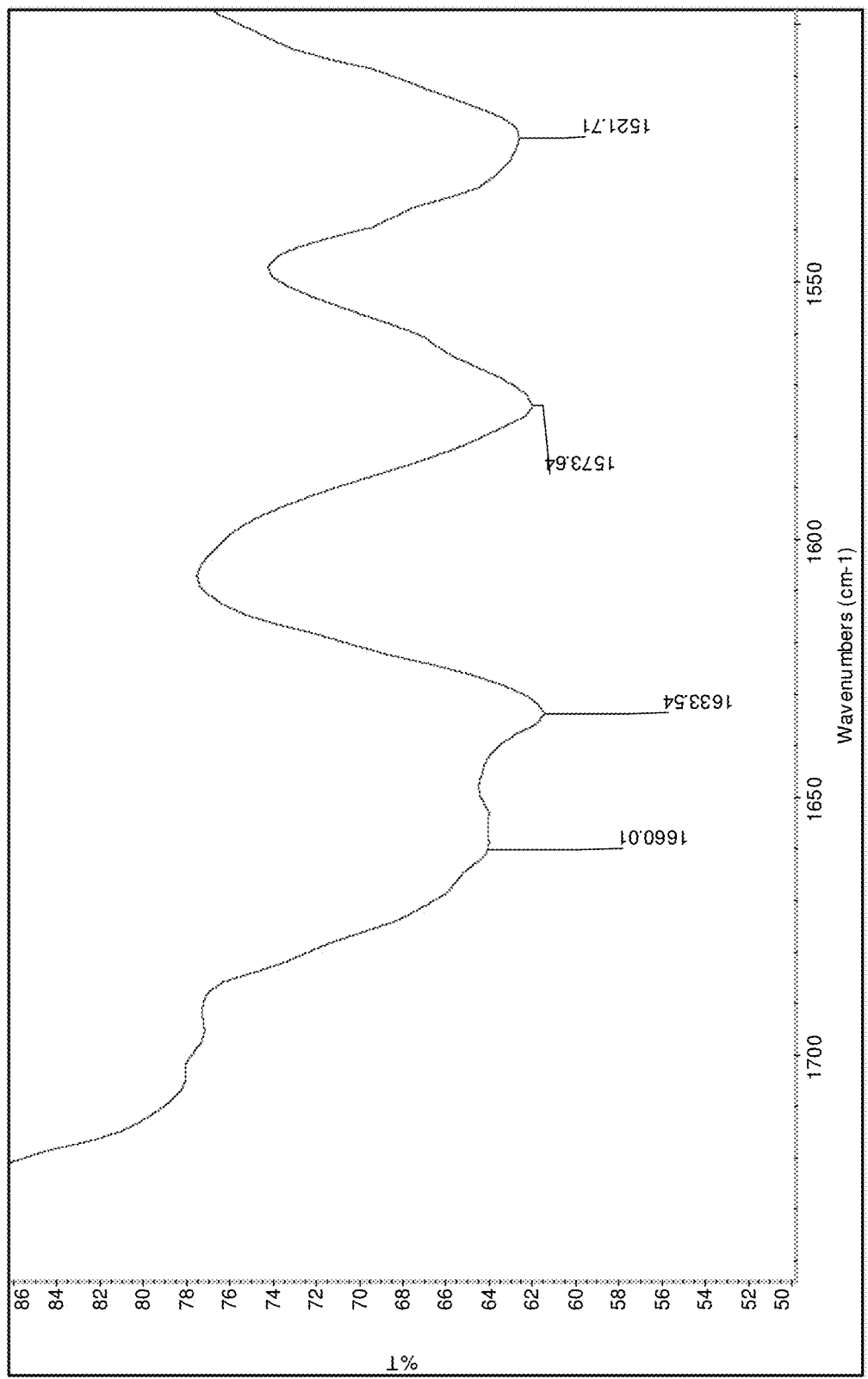
FIG. 4 is an IR spectrum of a free base of sepiapterin.
Figure 5:
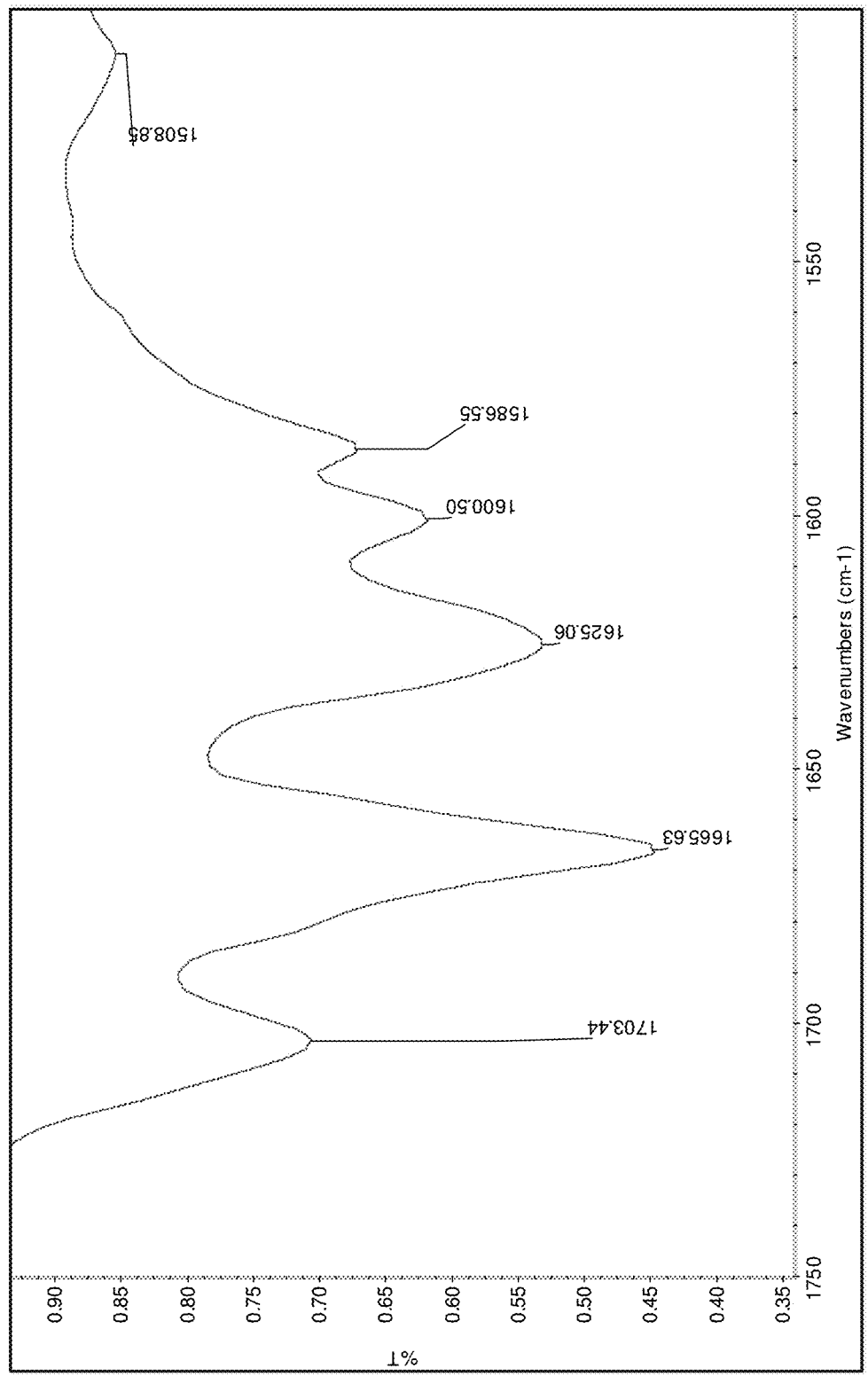
FIG. 5 is an IR spectrum of a hydrochloride salt and/or co-crystal of sepiapterin.
Figure 6:
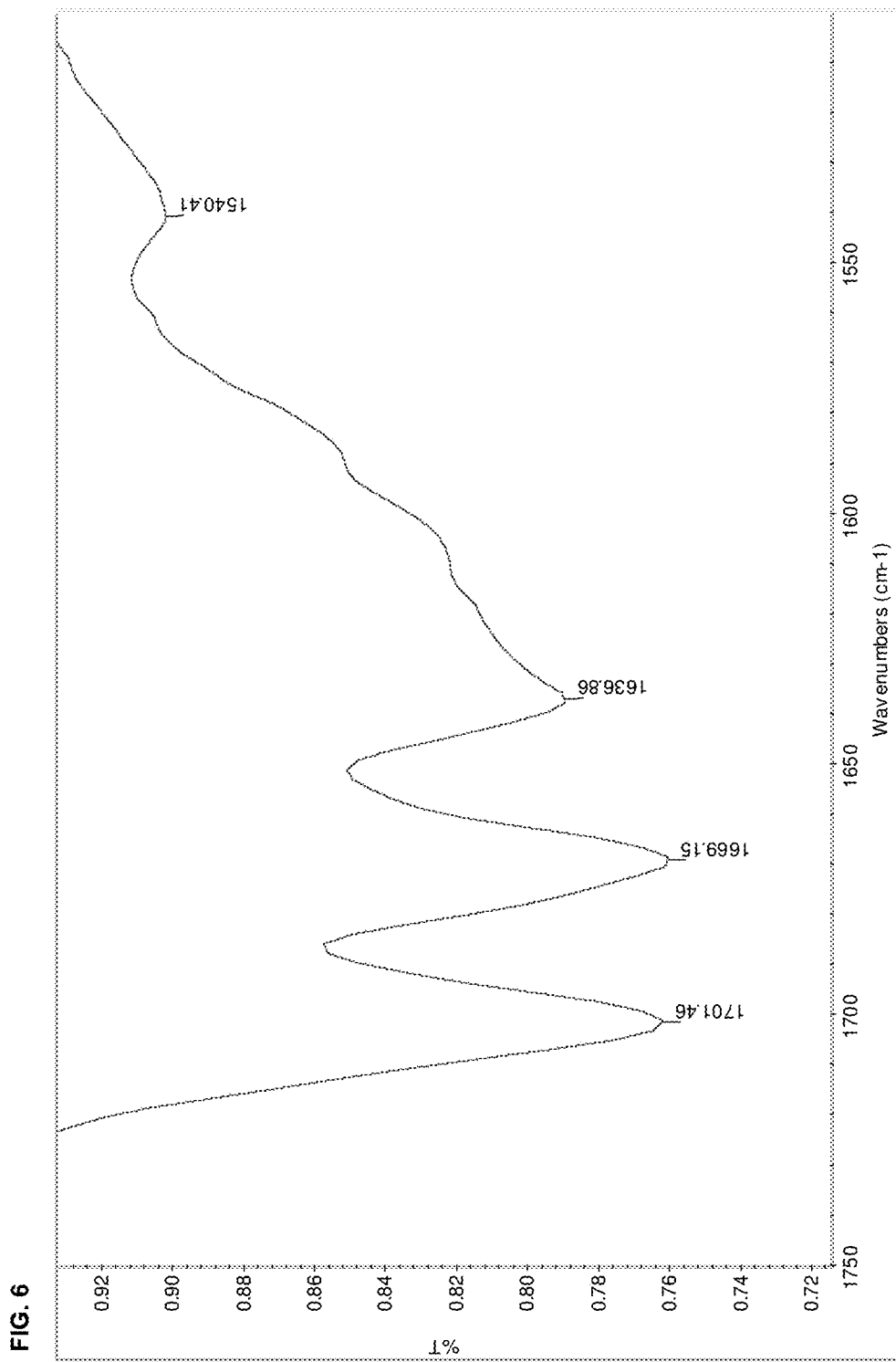
FIG. 6 is an IR spectrum of a methanesulfonate salt and/or co-crystal of sepiapterin.
Figure 7:
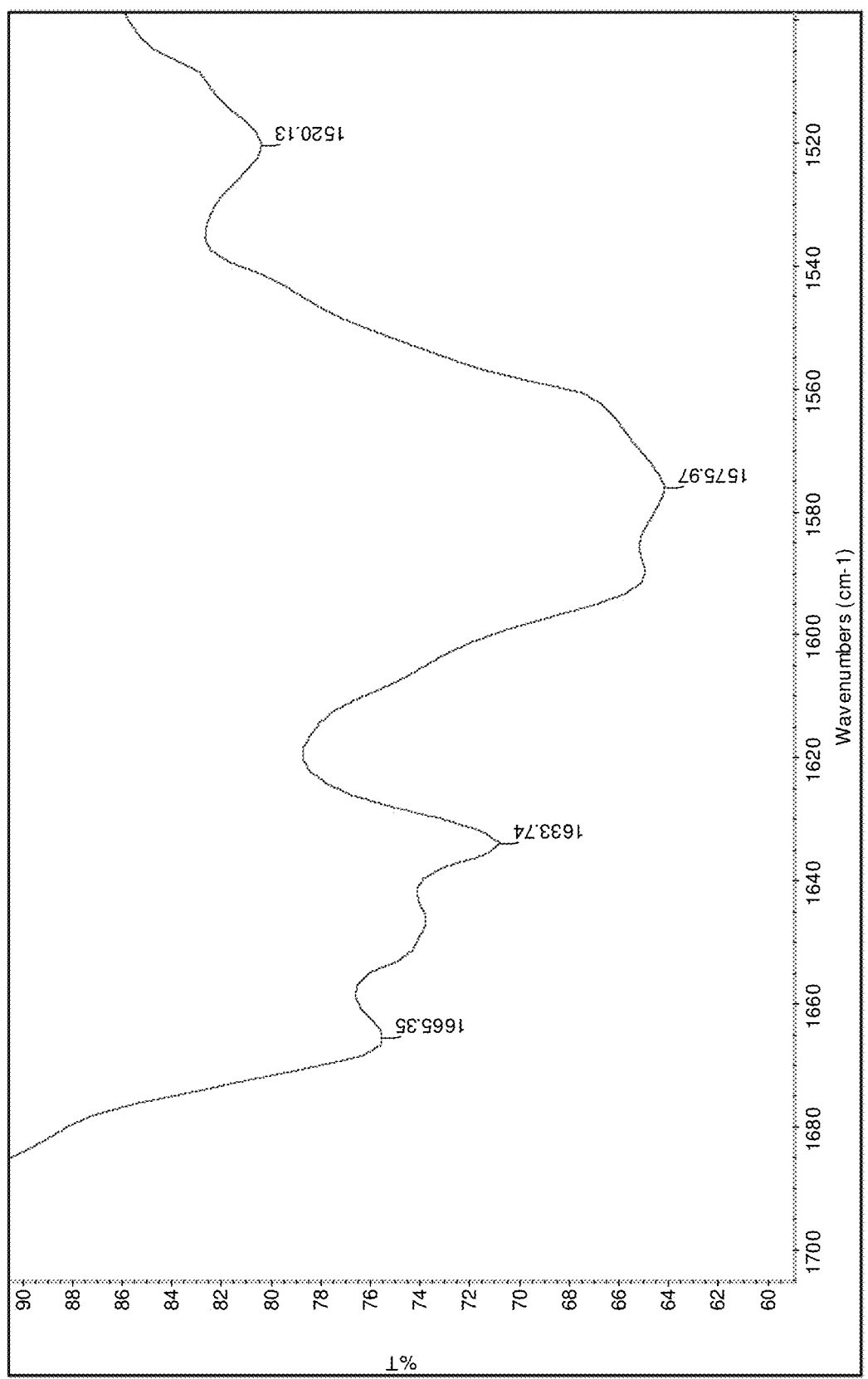
FIG. 7 is an IR spectrum of a nicotinate salt and/or co-crystal of sepiapterin.
Figure 8:
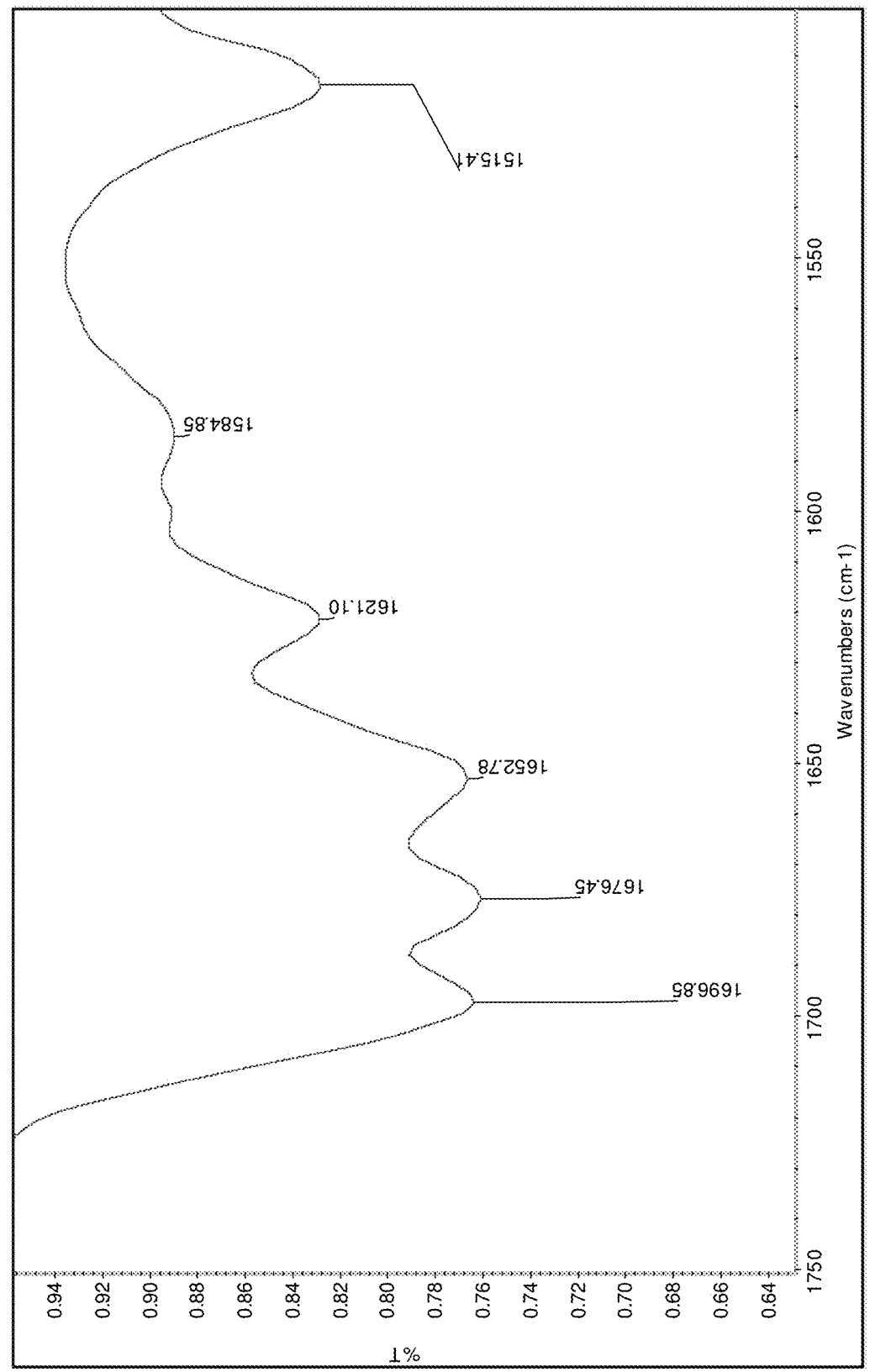
FIG. 8 is an IR spectrum of a toluenesulfonate salt and/or co-crystal of sepiapterin.
Figure 9:
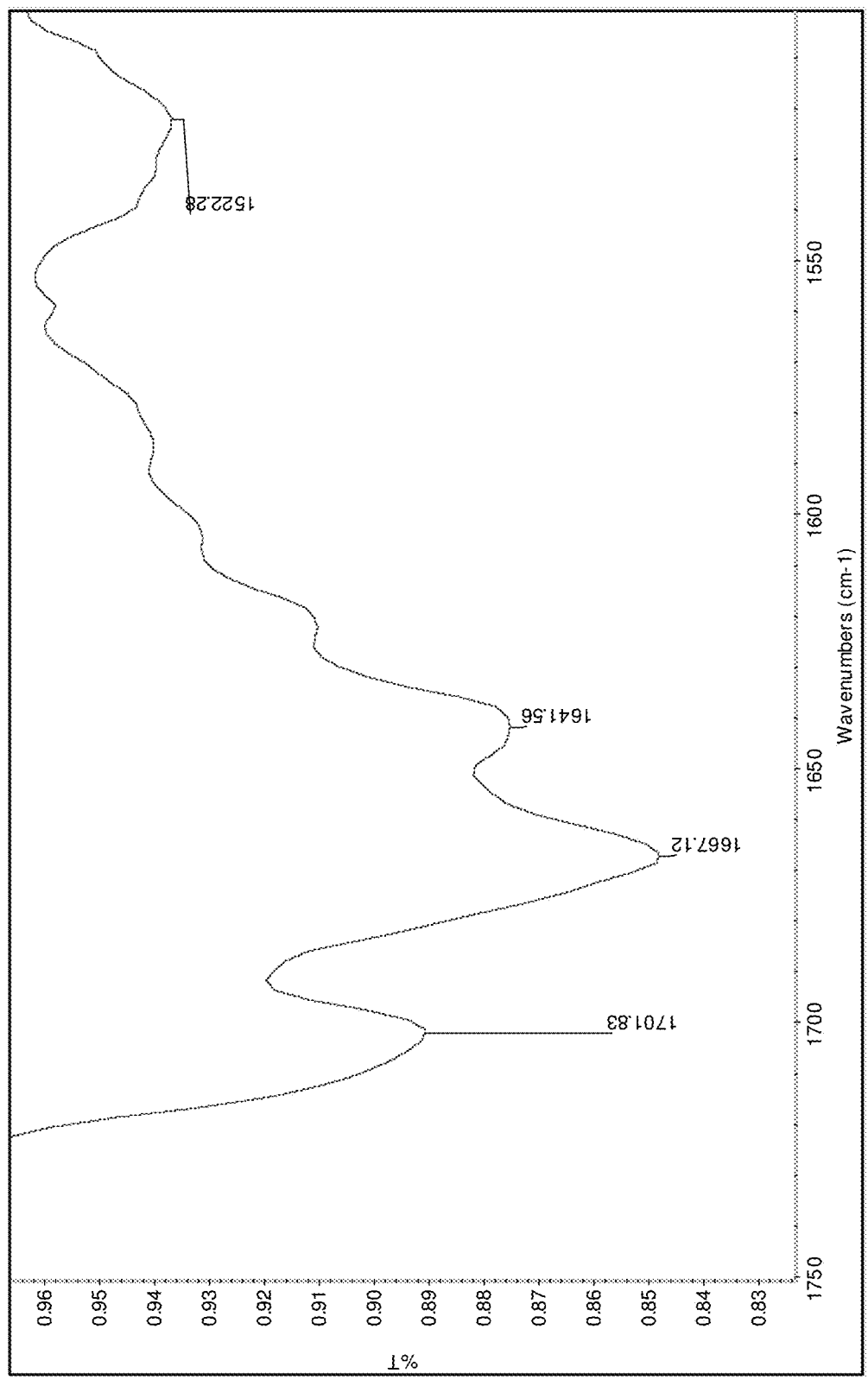
FIG. 9 is an IR spectrum of a benzenesulfonate salt and/or co-crystal of sepiapterin.
Figure 10:
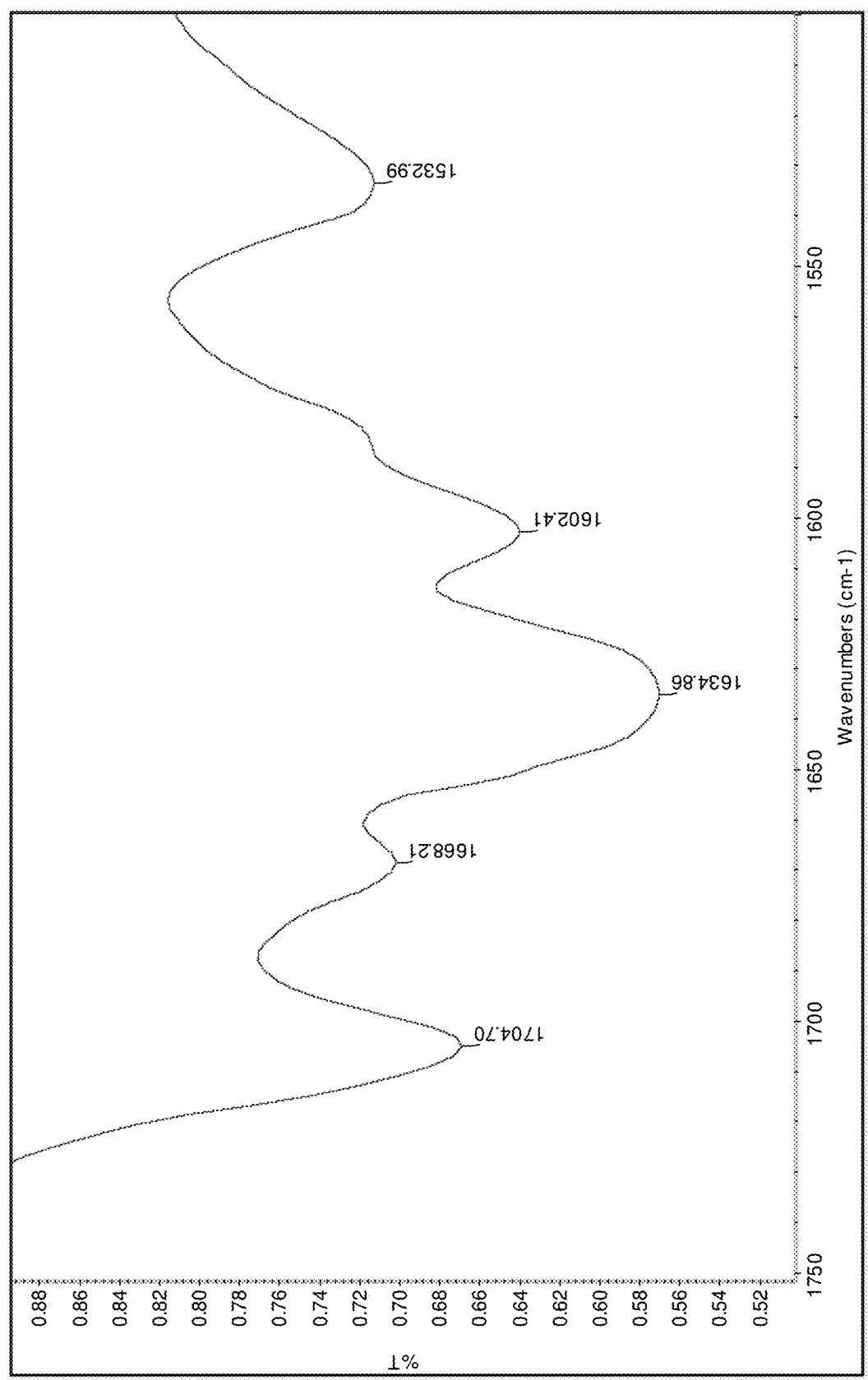
FIG. 10 is an IR spectrum of a sulfate salt and/or co-crystal of sepiapterin.
Figure 11:
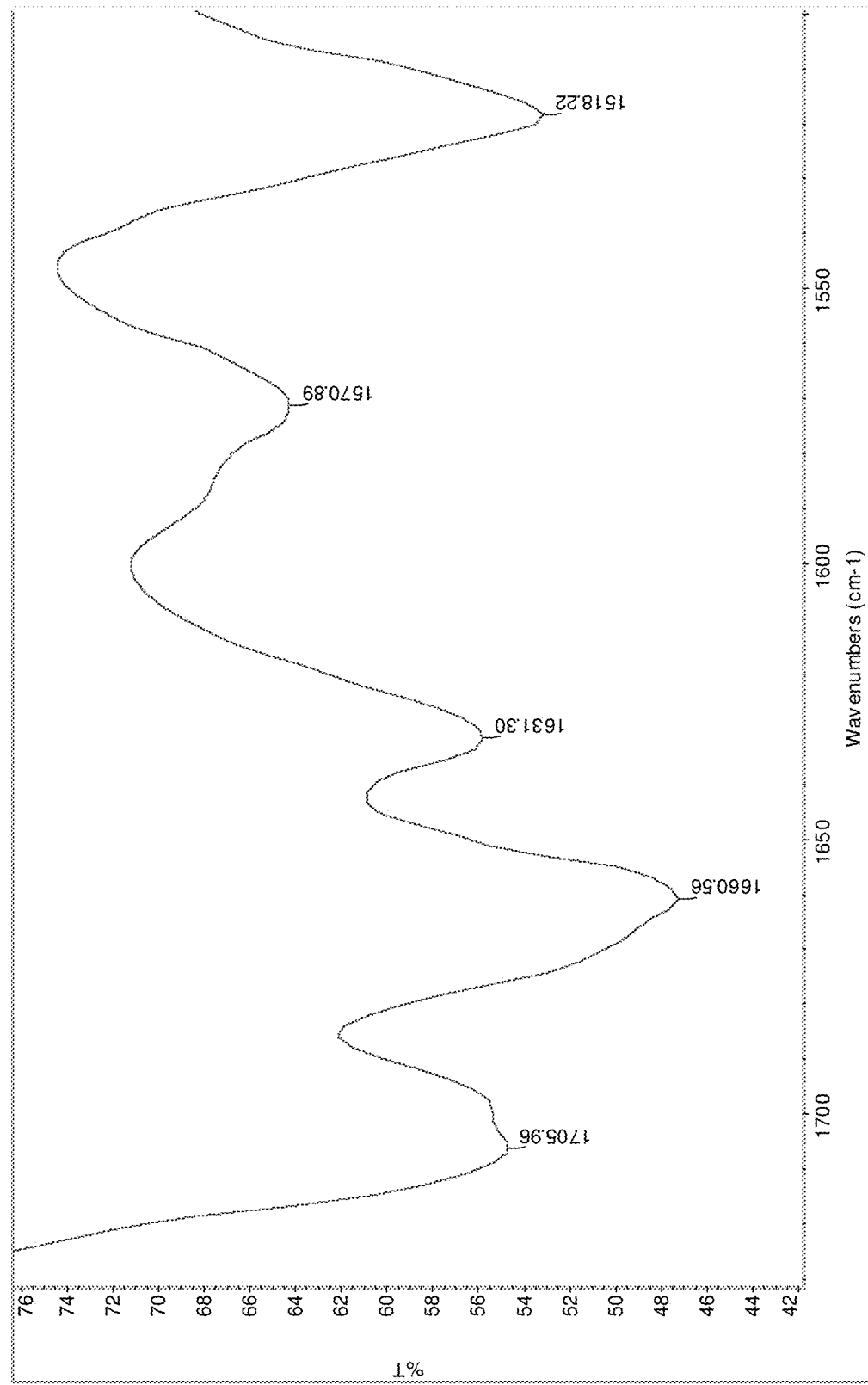
FIG. 11 is an IR spectrum of a phosphate salt and/or co-crystal of sepiapterin.
Figure 12:
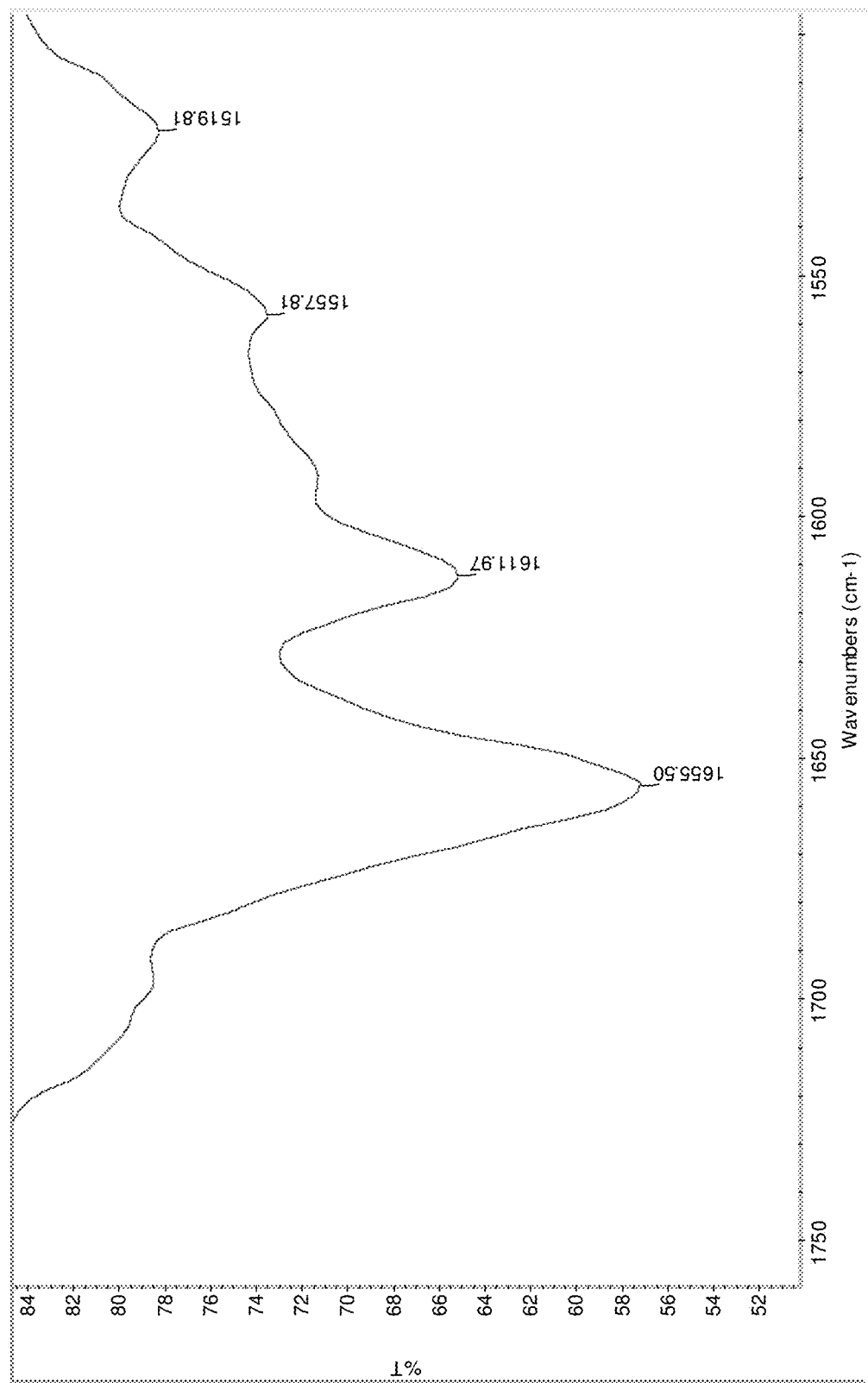
FIG. 12 is an IR spectrum of a L-tartrate salt and/or co-crystal of sepiapterin.
Figure 13:
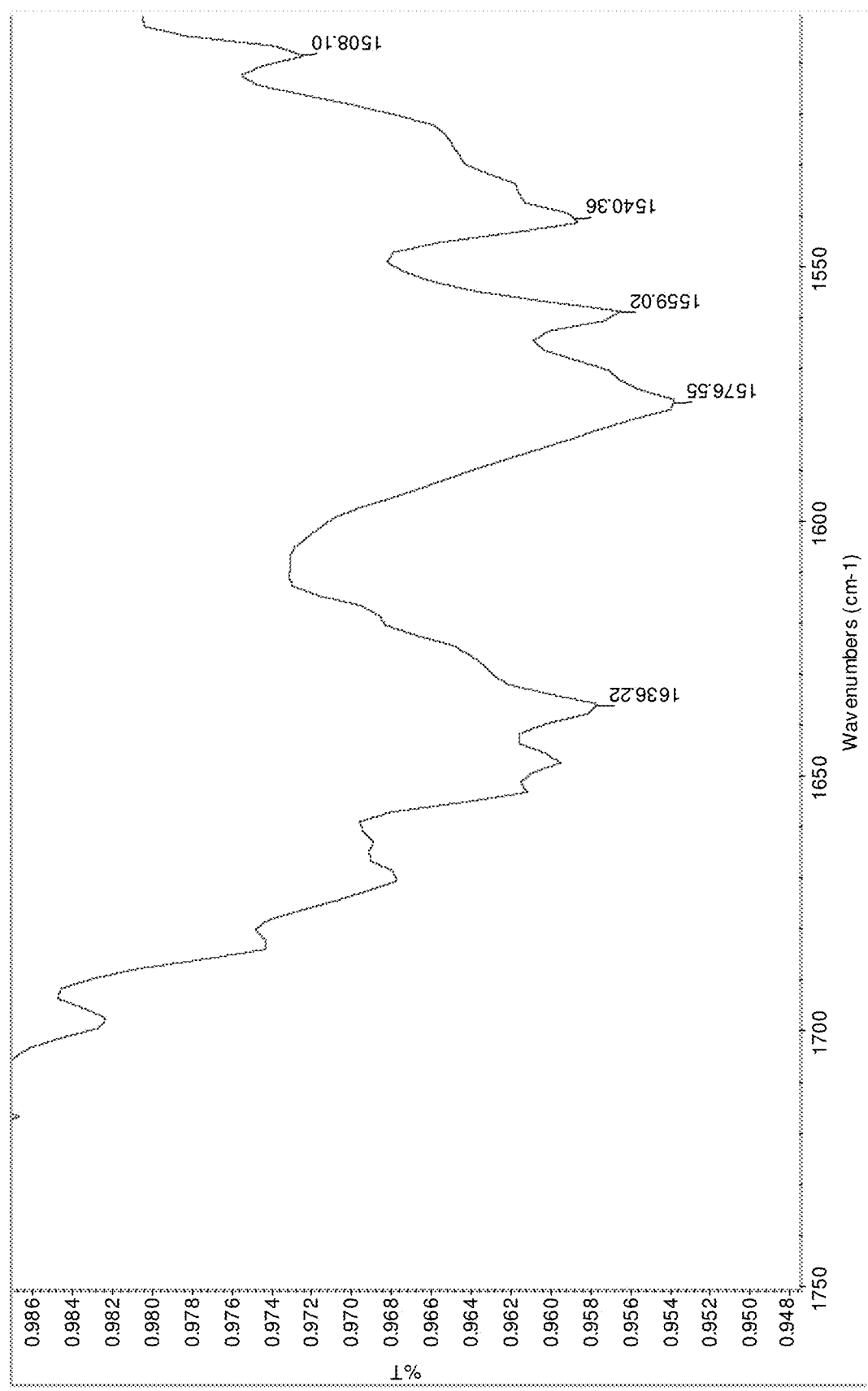
FIG. 13 is an IR spectrum of a glycolate salt and/or co-crystal of sepiapterin.
Figure 14:
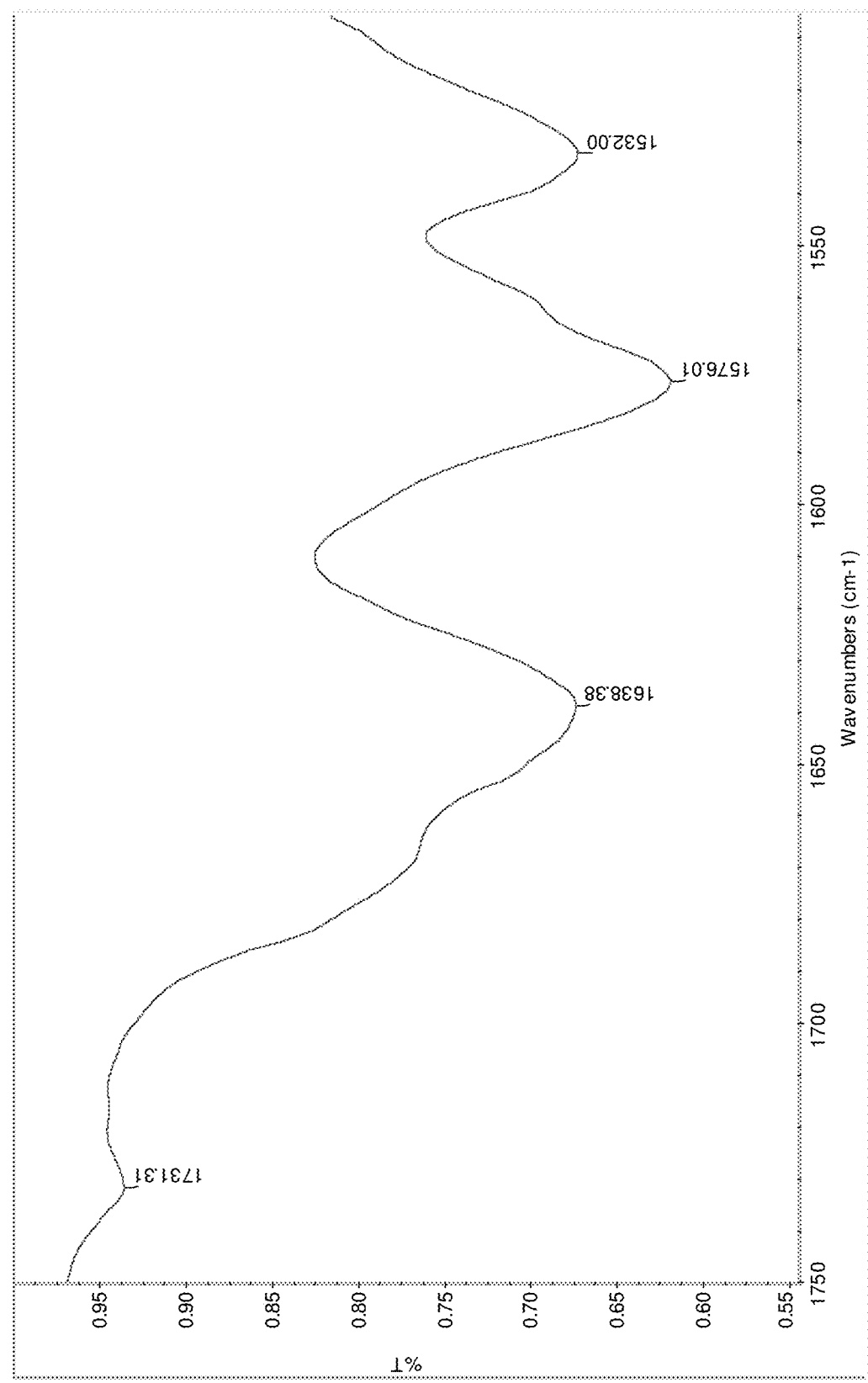
FIG. 14 is an IR spectrum of a malonate salt and/or co-crystal of sepiapterin.
Figure 15:
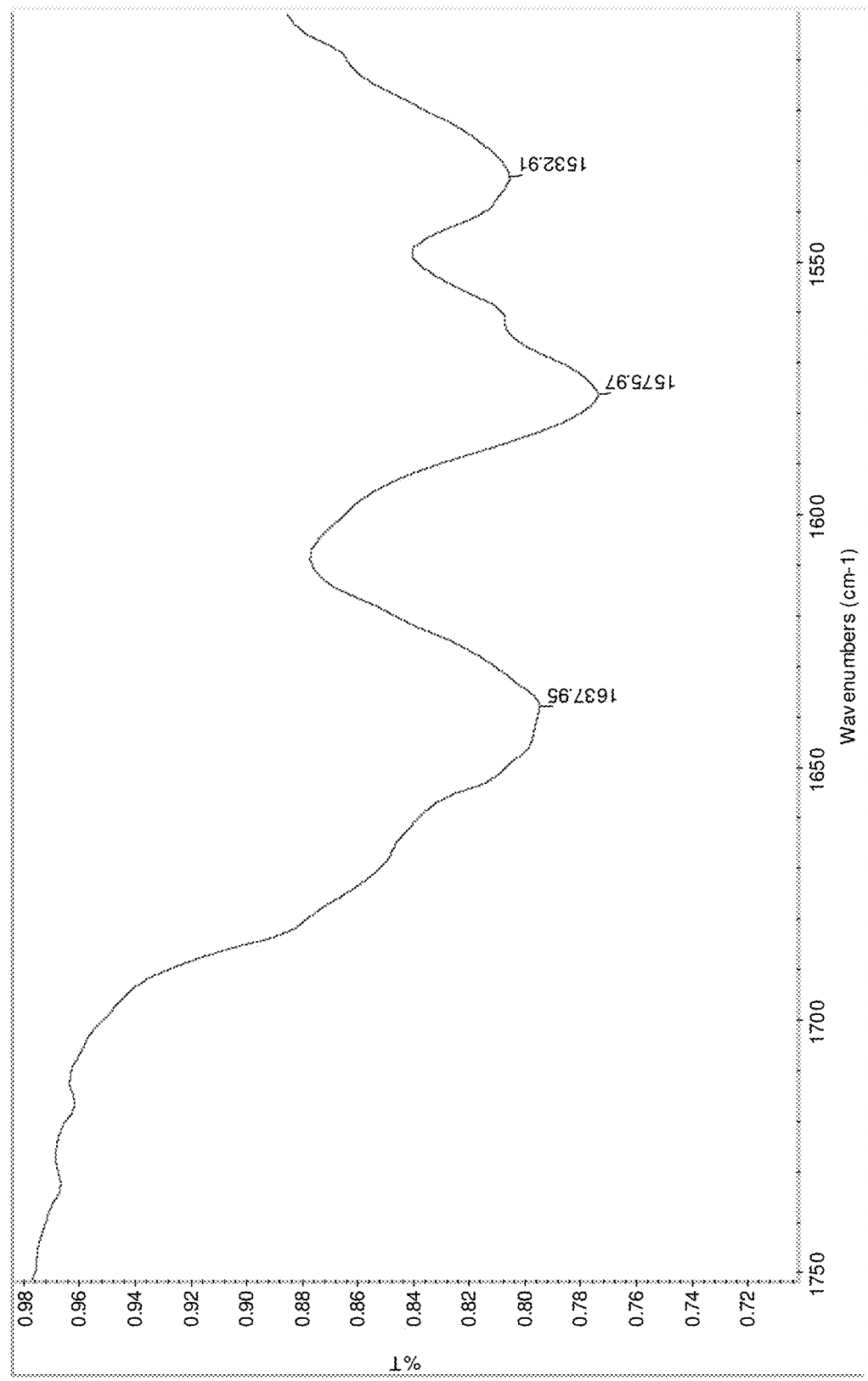
FIG. 15 is an IR spectrum of a gentisate salt and/or co-crystal of sepiapterin.
Figure 16:
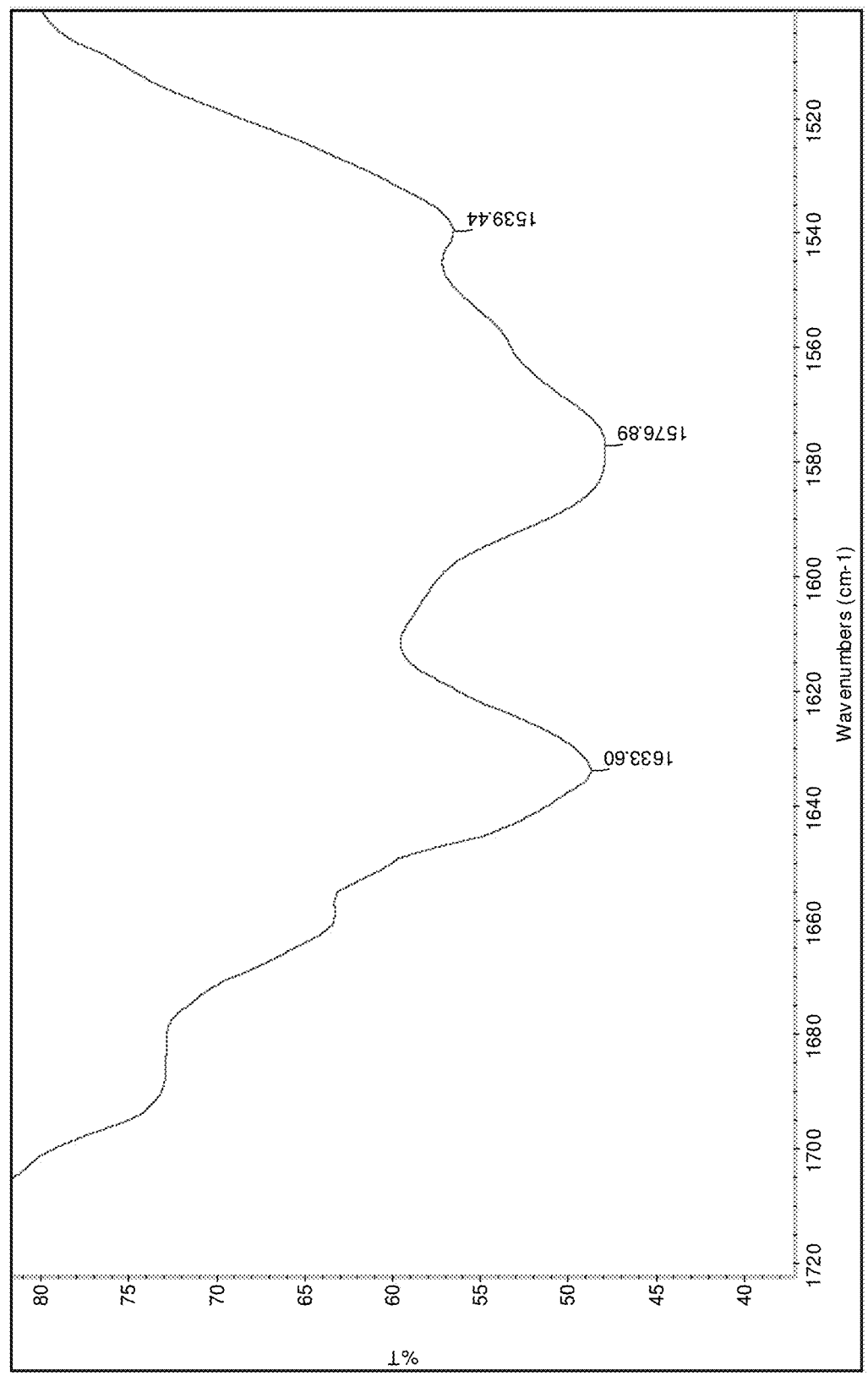
FIG. 16 is an IR spectrum of a fumarate salt and/or co-crystal of sepiapterin.

The present invention features pharmaceutical compositions including sepiapterin or a pharmaceutically acceptable salt and/or co-crystal thereof and methods for the treatment of tetrahydrobiopterin-related disorders with such compositions.

Compounds

Sepiapterin

The pharmaceutical compositions of the invention comprise sepiapterin, or a pharmaceutically acceptable salt and/or co-crystal thereof. Sepiapterin has the structure:

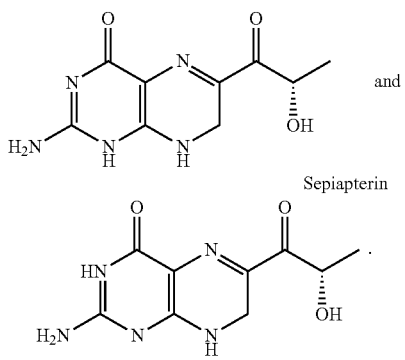

Sepiapterin

In some embodiments, sepiapterin or pharmaceutically acceptable salt and/or co-crystal thereof is present in a pharmaceutical composition of the invention in a crystalline form, as described herein.

In some embodiments of any of the foregoing compositions, sepiapterin is in crystalline form. In some embodiments, the crystalline form of sepiapterin has at least one peak at diffraction angle 2θ (°) of about 9.7°±0.5, about 10.2°±0.5, and/or about 11.3°±0.5 as measured by X-ray diffractometry by irradiation with Cu Kα X-rays or calculated from X-ray diffractometry.

In some embodiments, the crystalline form of sepiapterin is characterized by refractions at angles of refraction 2θ of at least about 9.7°, about 10.2°, about 11.3°, about 14.0°, about 14.6°, about 19.9°, about 22.2°, about 25.3°, and about 32.4°. In some embodiments, the crystalline form of sepiapterin is characterized by refractions at angles of refraction 2θ as set forth in Table 1. Alternatively, the sepiapterin, or a pharmaceutically acceptable salt and/or co-crystal thereof, is present in an amorphous form or a combination of crystalline forms or combination of at least one crystalline form and amorphous form.

In some embodiments, a pharmaceutical composition of the invention includes 20-30% sepiapterin or pharmaceutically acceptable salt and/or co-crystal thereof by total weight, e.g., 20%, 22%, 25%, 27%, or 30%. In some embodiments, a pharmaceutical composition includes greater than 20% sepiapterin or pharmaceutically acceptable salt and/or co-crystal thereof by total weight, e.g., greater than 25%, greater than 30%, greater than 40%, greater than 50%, greater than 60%, greater than 70%, greater than 80%, or greater than 90%.

Tetrahydrobiopterin

Sepiapterin, upon administration to a subject, is converted to tetrahydrobiopterin. Tetrahydrobiopterin has the structure:

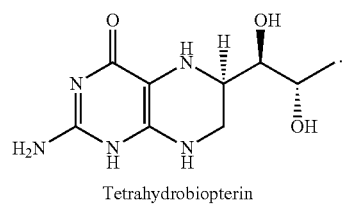

Tetrahydrobiopterin

Lactoylpterin

An impurity that may be present in sepiapterin preparations is lactoylpterin, which may result from oxidation of sepiapterin. Lactoylpterin has the structure:

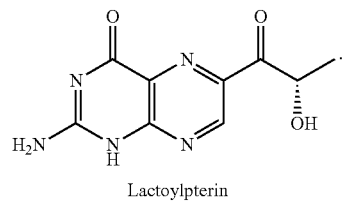 [SMILES: C[C@H](O)C(=O)c1cnc2[nH]c(N)nc(=O)c2n1]

Lactoylpterin

Excipients

Antioxidants

Sepiapterin is prone to rapid oxidation when exposed to air. Accordingly, a pharmaceutical composition of the invention may include an antioxidant. The antioxidant may minimize the oxidative degradation of sepiapterin. Examples of antioxidants include, but are not limited to, 4-chloro-2,6-di-tert-butylphenol, tocopherol, alpha-tocopherol, alkylated diphenylamines, ascorbic acid, ascorbyl myristate, ascorbyl palmitate, ascorbyl stearate, beta-carotene, butylated hydroxyanisole, butylated hydroxytoluene, citric acid, cysteine, D-alpha-tocopheryl polyethylene glycol 1000 succinate, deferoxamine methanesulfonate, dodecyl gallate, ethylparaben, folic acid, fumaric acid, gallic acid, glutathione, lecithin, malic acid, methylparaben, monothioglycerol, N-acetyl cysteine, nordihydroguaiaretic acid, octyl gallate, p-phenylenediamine, potassium ascorbate, potassium metabisulfite, potassium sorbate, propionic acid, propyl gallate, retinol, sorbic acid, sodium ascorbate, sodium bisulfite, sodium hydrosulfite, sodium isoascorbate, sodium metabisulfite, sodium sulfite, sodium thiosulfate, tartaric acid, tert-butylhydroquinone, tocopheryl acetate, vitamin A, vitamin B6, vitamin B12, or vitamin E. In some embodiments, a pharmaceutical composition of the invention includes ascorbic acid, tocopherol, retinol, ascorbyl palmitate, N-acetyl cysteine, glutathione, butylatedhydroxytoluene, and/or butylatedhydroxyanisole as antioxidant. In some embodiments, a pharmaceutical composition of the invention includes ascorbic acid, retinol, ascorbyl palmitate, N-acetyl cysteine, glutathione, butylatedhydroxytoluene, and/or butylatedhydroxyanisole as antioxidant.

In some embodiments, the pharmaceutical composition includes less than 10% antioxidant by weight, e.g., less than 9%, less than 8%, less than 7%, less than 6%, less than 5%, less than 4%, less than 3%, less than 2%, or less than 1%. In some embodiments, the pharmaceutical composition includes 2-9% antioxidant by total weight, e.g., 2-4%, 3-5%, 4-6%, 5-7%, 6-8%, or 7-9%. In some embodiments, the pharmaceutical composition includes 5-100% of the USP maximum daily dose of the antioxidant, e.g., in some embodiments, the pharmaceutical composition includes 5%, 10%, 15%, 20%, 30%, 40%, 50%, 60%, 70%, 80%, 90%, or 100% of the USP maximum daily dose of the antioxidant. In some embodiments, the ratio of sepiapterin or pharmaceutically acceptable salt and/or co-crystal thereof to antioxidant is at least 1:1, e.g., 2:1, 3:1, 4:1, 5:1, 6:1, 7:1, 8:1, 9:1, or 10:1 wt/wt. In some embodiments, the ratio of sepiapterin, or a pharmaceutically acceptable salt and/or co-crystal thereof, to antioxidant is greater than 4:1 (e.g., greater than 5:1, greater than 6:1, greater than 7:1, greater than 8:1, greater than 9:1, greater than 10:1, greater than 15:1, greater than 20:1) wt/wt. As previous formulations of sepiapterin included as much as 50% antioxidant (e.g., ascorbic acid) or more, it is surprising that compositions including less than 10% antioxidant or even no antioxidant are effective at stabilizing sepiapterin.

Dispersants

In some embodiments, a pharmaceutical composition of the invention includes at least one dispersant. The dispersant may cause particles in the formulation to separate, e.g., release their medicinal substances on contact with moisture. Examples of dispersant include, but are not limited to, crosslinked polyvinylpyrrolidone, carboxymethylcellulose (e.g., croscarmellose salt, e.g., croscarmellose sodium), starch (e.g., sodium starch glycolate), or alginic acid. In some embodiments, the dispersant in the pharmaceutical composition is a carboxymethylcellulose such as a pharmaceutically acceptable salt of croscarmellose. In some embodiments, the pharmaceutical composition may include 0.1-1.5% dispersant by total weight, e.g., 0.1%, 0.5%, 1%, or 1.5%. In some embodiments, the pharmaceutical composition includes less than 1.5% dispersant, e.g., less than 1%, less than 0.5%, or less than 0.1%.

Anti-Caking Agents

Sepiapterin has been found to clump when added to aqueous solutions. Anti-caking agents are often added to pharmaceutical compositions to prevent the formation of lumps, e.g., in solutions. Accordingly, in some embodiments, the pharmaceutical compositions of the invention include at least one anti-caking agent. In some embodiments, the pharmaceutical compositions include at least two anti-caking agents. Exemplary anti-caking agents include colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, and polydimethylsiloxane. In some embodiments, the at least one anti-caking agent is colloidal silicon dioxide or microcrystalline cellulose. In some embodiments, the pharmaceutical composition may include 65-75% anti-caking agent by total weight, e.g., 65%, 67%, 70%, 73%, or 75%. In some embodiments, the pharmaceutical composition includes both colloidal silicon dioxide and microcrystalline cellulose. In some embodiments, the pharmaceutical composition includes 60-65% microcrystalline cellulose by total weight and 5-7% colloidal silicon dioxide by total weight.

Dosing Vehicle

In some embodiments, a pharmaceutical composition of the invention is combined with a dosing vehicle prior to administration. In some embodiments of any of the foregoing compositions, the composition may be administered in a dosing vehicle with a viscosity of approximately 50-1750 centipoise (cP), e.g., to aid suspension and dosing of the pharmaceutical composition. One type of suspending agent that can be used is a combination of glycerin and sucrose in water (e.g., MEDISCA® oral mix with 2.5% glycerin and 27% sucrose in water). An appropriate quantity of composition can be added to the dosing vehicle mixture and agitated to suspend the composition just prior to administration.

Other suspending agents may also be used as a dosing vehicle. Exemplary suspending agents include agar, alginic acid, sodium carboxymethyl cellulose, carrageenan, dextrin, gelatin, guar gum, hydroxyethyl cellulose, hydroxypropyl cellulose, hypromellose, methyl cellulose, polyethylene glycol, povidone, tragacanth, xanthan gum, or other suspending agents known in the art.

Formulations

In some embodiments, the invention features a pharmaceutical composition including sepiapterin or pharmaceutically acceptable salt and/or co-crystal thereof and less than 10% by total weight of an antioxidant, e.g., 9%, 7%, 5%, 3%, 1%, 0.5%, 0.25%, or 0.1%. The antioxidant may be ascorbic acid. In some embodiments, the ratio of the sepiapterin or pharmaceutically acceptable salt and/or co-crystal thereof to the antioxidant is 1:1, e.g., 2:1, 5:1, 7:1, or 10:1 wt/wt. In some embodiments, the ratio of sepiapterin, or a pharmaceutically acceptable salt and/or co-crystal thereof, to antioxidant is greater than 4:1 (e.g., greater than 5:1, greater than 6:1, greater than 7:1, greater than 8:1, greater than 9:1, greater than 10:1, greater than 15:1, greater than 20:1) wt/wt. A pharmaceutical composition may include 20-30% sepiapterin or pharmaceutically acceptable salt and/or co-crystal thereof by total weight, e.g., 20%, 22%, 25%, 27%, or 30%. A pharmaceutical composition can further include a dispersant, e.g., croscarmellose sodium. The pharmaceutical composition may include 0.1-1.5% dispersant by total weight, e.g., 0.1%, 0.5%, 1%, or 1.5%. In some embodiments, a pharmaceutical formulation includes at least one anti-caking agent, e.g., colloidal silicon dioxide or microcrystalline cellulose. A pharmaceutical composition may include 65-75% anti-caking agent by total weight, e.g., 65%, 67%, 70%, 73%, or 75%. In some embodiments, a pharmaceutical composition includes both colloidal silicon dioxide and microcrystalline cellulose. In some embodiments, a pharmaceutical composition includes 60-65% microcrystalline cellulose by total weight and 5-7% colloidal silicon dioxide by total weight. In some embodiments, the sepiapterin or pharmaceutically acceptable salt and/or co-crystal thereof is formulated as particles less than 140 µm in size, e.g., 120 µm, 110 µm, 100 µm, 90 µm, 80 µm, 70 µm, 60 µm, 50 µm, 40 µm, 30 µm, 20 µm, 10 µm, or 5 µm. In some embodiments, a pharmaceutical composition includes less than 50%, e.g., less than 9%, less than 8%, less than 7%, less than 6%, less than 5%, less than 4%, less than 3%, less than 2%, less than 1.3%, or less than 1%, of an impurity such as lactoylpterin, e.g., the composition includes less than 0.9%, less than 0.8%, less than 0.7%, less than 0.6%, less than 0.5%, less than 0.4%, less than 0.3%, or less than 0.2%.

Sepiapterin, or a pharmaceutically acceptable salt and/or co-crystal thereof, may serve as a useful therapeutic for diseases associated with low intracellular BH4 levels or with dysfunction of various BH4 dependent metabolic pathways including, but not limited to, primary tetrahydrobiopterin deficiency, GTPCH deficiency, 6-pyruvoyl-tetrahydropterin synthase (PTPS) deficiency, DHPR deficiency, sepiapterin reductase deficiency, dopamine responsive dystonia, Segawa Syndrome, tyrosine hydroxylase deficiency, phenylketonuria, DNAJC12 deficiency, Parkinson's Disease, depression due to Parkinson's Disease, impulsivity in Parkinson's patients, major depression, Autism spectrum, ADHD, schizophrenia, Bipolar disorder, cerebral ischemia, restless leg syndrome, Obsessive Compulsive Disorder, anxiety, aggression in Alzheimer's disease, cerebrovascular disorders, spasm after subarachnoidal hemorrhage, myocarditis, coronary vasospasm, cardiac hypertrophy, arteriosclerosis, hypertension, thrombosis, infections, endotoxin shock, hepatic cirrhosis, hypertrophic pyloric stenosis, gastric mucosal injury, pulmonary hypertension, renal dysfunction, impotence, and hypoglycemia. Thus, the various forms of sepiapterin, or a pharmaceutically acceptable salt thereof, in accordance with the present invention can be administered to a patient in an effective amount to obtain a treatment or amelioration of the disease, disorder or condition.

In some embodiments, the sepiapterin is a salt and/or co-crystal of sepiapterin, wherein the salt and/or co-crystal is a salt and/or co-crystal of sepiapterin with sulfuric acid, p-toluene sulfonic acid, methane sulfonic acid, benzene sulfonic acid, malonic acid, tartaric acid (e.g., L-tartaric acid), phosphoric acid, gentisic acid, fumaric acid, glycolic acid, acetic acid, or nicotinic acid.

In some embodiments, the pharmaceutical composition comprises crystalline sepiapterin free base or pharmaceutically acceptable salt and/or co-crystal thereof. The crystalline sepiapterin free base or a crystalline form of a salt and/or co-crystal of sepiapterin can occur as an anhydrate (e.g., without having any bound water or solvent or hydration or solvation) or as a hydrate, a partial hydrate (e.g., hemihydrate, sesquihydrate), as a dihydrate, a trihydrate, wherein the crystalline form binds a water of hydration or a solvent molecule associated with the crystalline form of sepiapterin or salt thereof. In an embodiment, crystalline sepiapterin occurs as a monohydrate or as a hemihydrate.

The present invention provides a pharmaceutical composition including a pharmaceutically acceptable carrier and an effective amount, e.g., a therapeutically effective amount, including a prophylactically effective amount, of sepiapterin, or a salt and/or co-crystal thereof.

The pharmaceutically acceptable carrier can be any of those conventionally used and is limited only by chemico-physical considerations, such as solubility and lack of reactivity with the compound, and by the route of administration. It will be appreciated by one of skill in the art that, in addition to the following described pharmaceutical compositions; sepiapterin or pharmaceutically acceptable salt and/or co-crystal thereof can be formulated as inclusion complexes, such as cyclodextrin inclusion complexes, or liposomes.

The pharmaceutically acceptable carriers described herein, for example, vehicles, adjuvants, excipients, or diluents, are well known to those who are skilled in the art and are readily available to the public. It is preferred that the pharmaceutically acceptable carrier be one which is chemically inert to the active compounds and one which has no detrimental side effects or toxicity under the conditions of use.

Dosage

Sepiapterin or pharmaceutically acceptable salt and/or co-crystal thereof can be used in any suitable dose. Suitable doses and dosage regimens can be determined by conventional range finding techniques. Generally treatment is initiated with smaller dosages, which are less than the optimum dose. Thereafter, the dosage is increased by small increments until optimum effect under the circumstances is reached. For convenience, the total daily dosage may be divided and administered in portions during the day if desired. In proper doses and with suitable administration of certain compounds, the present invention provides for a wide range of responses. Typically, the dosages range from about 2.5 to about 150 mg/kg body weight of the patient being treated/day. For example, in embodiments, sepiapterin, or pharmaceutically acceptable salt and/or co-crystal thereof, may be administered from about 20 mg/kg to about 200 mg/kg, from about 40 mg/kg to about 150 mg/kg, from about 60 mg/kg to about 120 mg/kg, from about 80 mg/kg to about 100 mg/kg, from about 40 mg/kg to about 60 mg/kg, from about 2.5 mg/kg to about 20 mg/kg, from about 2.5 mg/kg to about 10 mg/kg, from about 2.5 mg/kg to about 5 mg/kg, of subject body weight per day, one or more times a day, to obtain the desired therapeutic effect.

In some embodiments, the dose is an amount sufficient to produce levels of BH4 in the CNS, e.g., as measured in the CSF and/or sufficient to produce a therapeutic result, e.g., increased levels of serotonin or dopamine in the CNS. In some embodiments, an increase in BH4 in the CNS (e.g., brain) is measured by determining the level of metabolites of a monoamine e.g., serotonin and/or dopamine (e.g., homovanillic acid or 5-hydroxyindoleacetic acid (5-HIAA)) in the CSF, wherein an increase of metabolites in the CSF indicates an increase in BH4 levels in the CNS (e.g., brain). In some embodiments, the dose is an amount sufficient to increase levels of BH4 at least two times greater than the levels of BH4 prior to administration as measured in the plasma or an organ of the subject, e.g., the liver of the subject.

In some embodiments, sepiapterin or pharmaceutically acceptable salt and/or co-crystal thereof can be formulated into unit solid oral dosage forms such as particles. In these embodiments, each unit solid oral dosage form can comprise any suitable amount of sepiapterin or pharmaceutically acceptable salt and/or co-crystal thereof. For example, each solid oral dosage form can comprise about 2.5 mg, about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg.

Routes of Administration

The choice of carrier will be determined in part by the particular active agent, as well as by the particular method used to administer the composition. Accordingly, there is a wide variety of suitable formulations of the pharmaceutical composition of the present invention. The following formulations for oral, aerosol, parenteral, subcutaneous, intravenous, intra-arterial, intramuscular, intraperitoneal, intrathecal, rectal, and vaginal administration are merely exemplary and are in no way limiting.

A pharmaceutical composition may be a liquid formulation, such as in the form of a solution, suspension, or emulsion. Formulations suitable for oral administration can consist of (a) capsules, tablets, lozenges, and troches, each containing a predetermined amount of the active ingredient, as solids or granules; (b) powders; (c) liquid solutions, such as an effective amount of the compound dissolved in diluents, such as water, saline, or orange juice; (d) suspensions in an appropriate liquid; and (e) suitable emulsions. Preferred are solid oral dosage forms such as capsule forms, tablet forms, and powder forms. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for oral and/or parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, benzyl alcohol, or hexadecyl alcohol, glycols, such as propylene glycol or polyethylene glycol and other polyethylene alcohols, glycerol ketals, such as 2,2-dimethyl-1,3-dioxolane-4-methanol, ethers, such as poly(ethylene glycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazopeak quaternary ammonium salts, and (3) mixtures thereof.

The parenteral formulations will typically contain from about 20 to about 30% by weight of sepiapterin or pharmaceutically acceptable salt and/or co-crystal thereof in solution. Suitable preservatives and buffers can be used in such formulations. In order to minimize or eliminate irritation at the site of injection, such compositions may contain one or more nonionic surfactants having a hydrophilic-lipophilic balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

A pharmaceutical composition may be an injectable formulation. The requirements for effective pharmaceutical carriers for injectable compositions are well known to those of ordinary skill in the art. See Remington: The Science and Practice of Pharmacy, (22nd ed.) ed. L. V. Allen, Jr., 2013, Pharmaceutical Press, Philadelphia, Pa.

Topical formulations, including those that are useful for transdermal drug release, are well-known to those of skill in the art and are suitable in the context of the invention for application to skin. Topically applied compositions are generally in the form of liquids, creams, pastes, lotions and gels. Topical administration includes application to the oral mucosa, which includes the oral cavity, oral epithelium, palate, gingival, and the nasal mucosa. In some embodiments, the composition contains sepiapterin, or a pharmaceutically acceptable salt thereof, and a suitable vehicle or carrier. It may also contain other components, such as an anti-irritant. The carrier can be a liquid, solid or semi-solid. In embodiments, the composition is an aqueous solution. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

A pharmaceutical composition may be an aerosol formulation to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Additionally, a pharmaceutical composition may be a suppository. Formulations suitable for vaginal administration may be presented as pessaries, tampons, creams, gels, pastes, foams, or spray formulas containing, in addition to the active ingredient, such carriers as are known in the art to be appropriate.

Solid Dosage Form for Oral Administration Formulations for oral use include particles containing the active ingredient(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, anti-adhesives (e.g., magnesium stearate, zinc stearate, stearic acid, silicas, hydrogenated vegetable oils, or talc), and anti-caking agents (e.g., colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, polydimethylsiloxane). Other pharmaceutically acceptable excipients can be colorants, flavoring agents, plasticizers, humectants, and buffering agents. In some embodiments, excipients (e.g., flavoring agents) are packaged with the composition. In some embodiments, excipients (e.g., flavorings) are packaged separately from the composition (e.g., are combined with the composition prior to administration).

The solid compositions of the invention may include a coating adapted to protect the composition from unwanted chemical changes, (e.g., chemical degradation prior to the release of the active substances). The coating may be applied on the solid dosage form in a similar manner as that described in Remington: The Science and Practice of Pharmacy, (22nd ed.) ed. L. V. Allen, Jr., 2013, Pharmaceutical Press, Philadelphia, Pa.

Powders and granulates may be prepared using the ingredients mentioned above in a conventional manner using, e.g., a mixer, a fluid bed apparatus, melt congeal apparatus, rotor granulator, extrusion/spheronizer, or spray drying equipment.

Methods of Treatment

The present invention features pharmaceutical compositions, e.g., in an orally tolerable formula, that contain a therapeutically effective amount of sepiapterin or pharmaceutically acceptable salt and/or co-crystal thereof, e.g., and less than 10% antioxidant. In some embodiments, the pharmaceutical composition is a granular formulation that is dispersed in a pharmaceutically acceptable carrier, for example the composition can be mixed into water, or other dosage vehicle, and ingested by a patient (e.g., over the course of 5 to 10 minutes). Suitable formulations for use in the present invention are found in Remington: The Science and Practice of Pharmacy, (22nd ed.) ed. L. V. Allen, Jr., 2013, Pharmaceutical Press, Philadelphia, Pa. Except insofar as any conventional carrier is incompatible with the active ingredient, its use in the pharmaceutical compositions is contemplated. Moreover, for animal (e.g., human) administration, it will be understood that preparations should meet sterility, pyrogenicity, general safety and purity standards as required by regulatory agencies.

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In some embodiments, patients receive 2.5 mg/kg/day, 5 mg/kg/day 10 mg/kg/day 20 mg/kg/day, 40 mg/kg/day, 60 mg/kg/day, or 80 mg/kg/day of sepiapterin, or a salt and/or co-crystal thereof. Patients may receive the pharmaceutical composition including sepiapterin, or a pharmaceutically acceptable salt and/or co-crystal thereof, once daily, twice daily or three times daily during treatment. In some embodiments, patients continue their other current medications for BH4-related disorder (e.g., L-dopa/carbidopa, 5HTP, melatonin, MAO inhibitors, and dopamine receptor agonists as prescribed) except for BH4 supplementation (if they are taking BH4). Patients may not be permitted to take any drugs known to inhibit folate synthesis (e.g., methotrexate, pemetrexed, or trimetrexate).

In some embodiments, patients taking BH4 therapy prior to study entry undergo a "washout" period during screening prior to administration of the pharmaceutical composition of the invention. Patients may be instructed to maintain a consistent diet, with respect to protein and phenylalanine (Phe) intake. Diet records may be reviewed by a qualified dietician. Total Phe concentrations for the 3-day period may be calculated by the dietician and recorded.

In some embodiments, patients who are taking BH4 discontinue administration of BH4 (i.e., BH4 washout). Blood samples for Phe concentrations may be obtained during the BH4 washout period at 7, 5, 3, and 1 day before the treatment with the pharmaceutical composition of the invention or until blood Phe levels are >360 μmol/L at any time point during BH4 washout. In some embodiments, pre-dose blood sample are tested for sepiapterin, Phe, BH4, and tyrosine (Tyr).

Methods of Producing Formulations

In some embodiments, a pharmaceutical composition of the invention may be produced by mixing sepiapterin or pharmaceutically acceptable salt and/or co-crystal thereof and an antioxidant with one or more excipients, e.g., a dispersant and one or more anti-caking agents. In some embodiments, each of the components of the composition are passed through a size exclusion filter (e.g., a filter having pores of 200 μm or less) prior to mixing. In some embodiments, the anti-caking agents are mixed together prior to the addition of the components (e.g., the sepiapterin, or a pharmaceutically acceptable salt and/or co-crystal thereof, dispersant, and antioxidant).

In some embodiments, the pharmaceutical composition is produced by:

(a) passing at least one anti-caking agent through a size exclusion filter (e.g., a filter having pores less than 200 μm);

(b) combining the sepiapterin, or a pharmaceutically acceptable salt and/or co-crystal thereof, antioxidant, and optionally a dispersant with the at least one anti-caking agent (e.g., by mixing in a blender); and (c) passing the combination of step b through a size exclusion filter (e.g., a filter having pores less than 150 μm).

In some embodiments, the at least one anti-caking agent of step a includes more than one anti-caking agent (e.g., two anti-caking agents) that have been mixed together prior to be passed through the size exclusion filter.

Examples

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention. As such, the following examples are provided to teach various aspects of the present invention. These examples represent individual embodiments of the aspects of this invention and one skilled in the art will recognize that additional examples can be generated in order to equally teach the aspects of the present invention.

Example 1. Preparation of a Pharmaceutical Composition Including Sepiapterin and an Antioxidant The process associated with the manufacture of a pharmaceutical composition including sepiapterin and less than 10% by total weight of an antioxidant was as follows:

1. Sepiapterin (0.34 kg), ascorbic acid (0.071 kg), microcrystalline cellulose (0.85 kg), croscarmellose sodium (0.14 kg), and colloidal silicon dioxide (0.085 kg) were individually sifted through a 140 mesh screen.
2. The colloidal silicone dioxide was mixed with microcrystalline cellulose, and the combined material was passed through an 80 mesh screen.
3. The screened material of step 2 was charged into a V-blender.
4. The filtered croscarmellose, ascorbic acid, and sepiapterin were added into the V-blender.
5. The contents of the V-blender were mixed for at least 10 minutes.
6. The mixture was sifted through a 140 mesh screen.
7. The mixture was stored at −20° C.

Example 2. Preparation of Pharmaceutical Composition Including Sepiapterin and an Antioxidant in a Dosing Vehicle The composition prepared in Example 1 (180 mg/kg of sepiapterin) was added to an amount of Medisca® oral mix (2.5% (w/w) glycerin, 27% (w/w) sucrose in water) sufficient to produce a 58.3 mg/mL concentration of sepiapterin.

Example 3. In Vivo Pharmacokinetic Analysis of Pharmaceutical Compositions of the Invention A total of eighteen CD-1 mice were assigned to 2 groups as summarized below. Each test article was evaluated at one dose level (180 mg/kg). All animals in each group received a single oral (PO) administration of one dose level of the test or control article. Doses (mg/kg) were calculated based on animal body weight. Nine male mice were in each group. Group 1 was administered sepiapterin added to a citric acid buffer solution including 750 mg sodium metabisulfite, 639 mg sodium citrate, 2.69 g of anhydrous citric acid, and 750 mg ascorbic acid in 300 mL of sterile water. 1.5 grams of carboxymethylcellulose was then added and stirred until dissolved. Sepiapterin (180 mg/kg) was added to the buffer to provide a concentration of 27 mg/mL. Group 1 mice were administered a dose volume of 6.67 mL/kg. Group 2 was administered the formulation prepared in Example 2. Group 2 mice were administered a dose volume of 3.086 mL/kg.

All animals were weighed prior to dose administration. Doses were administered as a single oral (PO) dose via oral gavage on Day 1. Doses were administered on a mg/kg basis. Animals were not fasted prior to dose administration.

Blood samples were collected into $K_2$EDTA tubes and stored on wet ice protected from light. Blood was processed to plasma by centrifugation (3500 rpm at 5° C.) within 30 minutes of collection. Plasma samples were placed into a tube along with a volume of 10% ascorbic acid in water. For every 0.1 mL of plasma, 11.1 μL of 10% ascorbic acid was added. Plasma tubes were pre-filled with 33.3 μL of 10% ascorbic acid assuming 0.3 mL of plasma was to be obtained from each sample. In the event the plasma sample was lower than 0.3 mL, the amount of additive was to be adjusted and noted (i.e., add 1 g of ascorbic acid to every 10 mL of water). All samples were transferred into separate 96 well plates (matrix tubes) and stored at −80° C. until shipped for analysis.

Sepiapterin in mouse tissue was analyzed by reversed-phase HPLC coupled with fluorescence and electrochemical detection respectively. Analytes in samples were stabilized by addition of ascorbic acid, dithioerythritol (DTE), and diethylenetriaminepentaacetic acid (DETAPAC). Sample preparation involved precipitation of proteins in perchloric acid containing the stabilizers and recovery of the clear supernatant following centrifugation.

Chromatography for Sepiapterin: Separation was achieved using a Phenomenex SphereClone 5 μm ODS(1) 250×4.6 mm LC column maintained at 35° C. during analysis. Separation was achieved isocratically using 25 mM potassium phosphate buffer, pH 4.0 with 17.5% methanol at a flow rate of 1.0 mL/min. Sepiapterin was detected using its natural fluorescence (Ex 425 nm; Em 530 nm). Lower limit of detection is 150 fmol on column with linearity being maintained to at least 20 pmol.

Each sample was split into two samples and analyzed on sequential days. An adjustment was made for dilution. Individual data, both raw and adjusted, and mean plasma concentrations (nM) were reported for each group and timepoint in FIG. 1. As shown in FIG. 2, concentrations of sepiapterin in the plasma were greater for the formulation of Example 2 than the formulation of sepiapterin in a citric acid buffer.

Example 4. Determination of BH4 Levels Produced by Pharmaceutical Compositions of the Invention Animals were administered the test items, sepiapterin or BH4, at dose levels of 20, 60 or 180 mg/kg. Blood, liver, kidney and urine samples (where possible) were collected from 3 animals/timepoints/group on the day of dosing at 0 (pre-dose, controls only), 0.5, 1, 2, 4, and 8 hours post-dose. Samples were assayed for sepiapterin or BH4 (not quantified in plasma) and non-compartmental pharmacokinetic analysis was performed. A summary of selected pharmacokinetic parameters in each matrix is presented in FIG. 3.

The pharmacokinetic evaluations revealed that the maximum sepiapterin plasma concentrations were observed 30 minutes or 2 hours post-dose with a secondary peak of absorption at the low- and mid-dose levels at 8 hours post-dose. Sepiapterin was detected in the liver and kidney only at 30 minutes post-dose and only in the liver for the mid- or high-dose. In urine, following sepiapterin administration, sepiapterin Cmax was observed 30 min post-dose at the mid- and high-dose levels and at the last timepoint in the low-dose group and was observed up the last timepoint where at least one sample was obtained. Sepiapterin exposure was the highest in urine amongst the analyzed matrices and increased in a less than dose proportional manner over the entire dose range in each urine, liver and kidney. Circulating sepiapterin exposure through plasma showed non-linear kinetics being much greater than dose proportional over the entire dose range, suggesting possible saturation kinetics in the plasma with increased dose levels, low distribution of sepiapterin in the tissues, and high level of excretion through urine.

BH4 liver and kidney Cmax was generally observed between 30 minutes and 2 hours post-dose and from 2 to 8 hours in urine, with no relationship to dose or treatment. At a given dose level, liver BH4 Cmax was roughly 2 to 4-fold higher following sepiapterin administration than BH4 alone, and was similar following both treatments in kidney, except at the high-dose where it was roughly 2-fold higher following sepiapterin administration. High inter-individual variability and sparse sampling in urine prevented a clear conclusion on urine exposure to BH4 following both treatments. Following sepiapterin or BH4 treatment, kidney, liver and urine exposure to BH4 decreased as the dose level increased, suggestive of non-linear BH4 kinetics in these matrices. The apparent BH4 elimination half-life was 2.5 hours in the kidney at the mid-dose following either treatment.

Example 5. In Vivo Evaluation of Pharmaceutical Compositions of the Invention in Humans A phase 1/2, open-label, randomized parallel arm, intra-patient dose titration study may be used to evaluate the safety, pharmacokinetics, and preliminary efficacy of the formulation of Example 2 in adult and adolescent primary tetrahydrobiopterin deficient subjects with hyperphenylalaninemia.

After consenting to the study, subjects will undergo screening procedures which include medical/surgical history, demographics, vital signs, ECG, physical examination, and clinical laboratory tests (chemistry, hematology, urinalysis). Blood Phe levels will be measured at screening and compared to the 3 most recent historical Phe concentrations to demonstrate that the Phe level obtained at screening is reflective of the previous 3 values. Subjects who are eligible based on screening tests will proceed to the BH4 washout period.

Eligible subjects who are taking BH4 [Kuvan® (sapropterin dihydrochloride)] will discontinue the medication during the BH4 washout period and will remain off this medication during the entire study. Subjects will be instructed to maintain a consistent diet (with respect to protein and Phe intake) and 3-day diet records will be collected during BH4 washout and throughout the study. On Days −7, −5, −3, and −1 during the BH4 washout period, blood will be collected for determination of Phe concentrations. If the Phe concentration is >360 μmol/L at any point during the 7-day BH4 washout, subjects will be eligible for randomization in the study. Subjects that do not reach a Phe concentration >360 μmol/L during the 7-day BH4 washout will not be eligible for study entry.

Subjects will receive treatment with sepiapterin for a total of 14 days (i.e., two 7-day treatment periods separated by a 3- to 4-day washout). Subjects will be randomized into one of 2 cohorts, with each cohort assessing 2 dose levels of the formulation of Example 2 via intra-subject titration.

Cohort 1, subjects will receive 2.5 mg/kg/day for 7 days in Period 1, undergo a 3- to 4-day washout period, then escalate to 10 mg/kg/day for 7 days in Period 2 (14 days total treatment)

Cohort 2, subjects will receive 5 mg/kg/day for 7 days in Period 1, undergo a 3- to 4-day washout period, then escalate to 20 mg/kg/day for 7 days in Period 2 (14 days total treatment).

Subjects will be eligible for dose escalation during Period 2 only if they meet the criteria for intrasubject dose escalation.

During the study, subjects will continue receiving their other current medications for PBD (including L-dopa/carbidopa, 5HTP, melatonin, MAO inhibitors, and dopamine receptor agonists as prescribed) except for BH4 supplementation (if they were taking BH4), and will be monitored clinically as per standard of care for PBD to optimize treatment.

Safety and tolerability will primarily be assessed by adverse events (AEs), vital signs, and clinical laboratory tests including chemistry, hematology, and urinalysis, physical examinations, and 12-lead electrocardiograms (ECGs). Preliminary efficacy will be assessed by the reduction in plasma Phe levels. Other secondary measures will include whole blood serotonin, serum prolactin and BH4, and urine sepiapterin, BH4 and neopterin.

Blood samples will be collected to characterize the pharmacokinetics of sepiapterin and its effect on serum BH4, Phe, and Tyr at the following time points for each dose level: on Day 1 at pre-dose (within 30 min of dosing), ±0.5 hr (±3 min), ±1 hr (±5 min), ±2 hr (±6 min), ±4 hr (±20 min), ±6 hr (±30 min), ±12 hr (±60 min, prior to Day 1 evening dose), and ±24 hours (±2 hr, prior to Day 2 morning dose) after the first dose of study drug; and on Day 7 (prior to the last dose of study drug).

Subjects will receive treatment with the formulation of Example 2 for a total of 14 days (i.e., two 7-day treatment periods separated by a 3- to 4-day washout), unless they meet criteria for stopping the formulation of Example 2 treatment.

Example 6. Preparation of Salts and/or Co-Crystals of Sepiapterin

Salts and/or co-crystals of sepiapterin and hydrochloric acid, methanesulfonic acid, toluenesulfonic acid, benzenesulfonic acid, nicotinic acid, sulfuric acid, phosphoric acid, malonic acid, L-tartric acid, fumaric acid, gentisic acid, and glycolic acid were produced by slurrying the free base of sepiapterin and the acid in acetone/water (9/1, v/v) or methanol for 2-17 days.

The salts and/or co-crystals were analyzed by DSC, TGA, HPLC, IR, and XRPD. The results are summarized in Table 19 below. The IR spectra are shown in FIGS. 4-16.

TABLE 19

Summary of sepiapterin salt and/or co-crystal analysis

| Salt form | Weight (mg) | TGA Weight loss (%) | DSC Endotherm (° C., onset) | Purity (%) | Molar ratio (FB:acid) | Residual solvent |
|---|---|---|---|---|---|---|
| HCl Salt | 190.9 | 3.6 | 218.3 | 93.94 | 1:1.3 | Negligible Acetone |
| Methanesulfonate | 188.0 | 4.23 | 182.3 | 91.14 | 1:1.0 | Negligible MeOH |
| Nicotinate | 246.0 | 1.27 | 220.4 | 97.16 | 1:0.9 | None |
| Toluenesulfonate | 256.4 | 0.5 | 190.3, 262.9 | 96.84 | 1:1.0 | None |
| Benzenesulfonate | 173.3 | 1.54 | 192.7, 206.2 | 90.20 | 1:1.0 | Negligible MeOH |
| Sulfate | 227.5 | 2.6 | 196.5 | 97.33 | 1:0.6 | None |
| Phosphate | 235.8 | 11.2 | 144.0, 206.8 | 96.75 | 1:1.1 | None |
| Malonate | 95.8 | 3.83 | 175.1 | 99.45 | TBD | None |
| L-Tartrate | 232.2 | 1.14 | 156.5, 174.6 | 99.75 | 1:1.0 | Negligible Acetone |
| Fumarate | 217.3 | 4.81 | 77.3, 132.8, 190.1 | 99.46 | 1:0.6 | Negligible Acetone |
| Gentisate | 98.1 | 6.92 | 83.2, 133.8, 149.0 | 94.35 | 1:0.5 | None |
| Glycolate | 135.4 | 20.15 | 79.3, 90.0, 132.3, 151.6 | 99.19 | 1:0.3 | None |

FB = free base

Example 7. Stability Analysis of Salts and/or Co-Crystals of Sepiapterin

The stability of the prepared salts and/or co-crystals was analyzed after 1 week at 25° C. and 60% relative humidity and 40° C. and 75% relative humidity. The results are summarized in Table 20 below. Surprisingly, of all the salts and/or co-crystals tested, the phosphate salt and/or co-crystal, the tartrate salt and/or co-crystal, and the nicotinate salt and/or co-crystal were noticeably more stable than the others. None of the phosphate, tartrate, or nicotinate salts and/or co-crystals underwent a form change during the stability testing, and each of them retained greater than 97% purity over the two weeks of the study. In fact, both the tartrate and nicotinate both retained greater than 99% purity.

TABLE 20

Summary of stability study results

| Salt | Time point | Condition | Form change | Purity (Area %) | Purity vs. initial (%) |
|---|---|---|---|---|---|
| Phosphate | Initial | NA | NA | 96.75 | NA |
| | 1 week | 25° C./60% RH | No | 95.35 | 98.6 |
| | | 40° C./75% RH | No | 95.91 | 99.1 |
| | 2 weeks | 25° C./60% RH | No | 95.87 | 99.1 |
| | | 40° C./75% RH | No | 94.50 | 97.7 |
| L-Tartrate | Initial | NA | NA | 99.75 | NA |
| | 1 week | 25° C./60% RH | No | 98.61 | 99.9 |
| | | 40° C./75% RH | No | 99.06 | 99.3 |
| | 2 weeks | 25° C./60% RH | No | 99.39 | 99.6 |
| | | 40° C./75% RH | No | 99.00 | 99.3 |
| Glycolate | Initial | NA | NA | 99.19 | NA |
| | 1 week | 25° C./60% RH | Glycolate and free base | 98.93 | 99.7 |
| | | 40° C./75% RH | Glycolate and free base | 98.54 | 99.3 |
| | 2 weeks | 25° C./60% RH | Glycolate and free base | 98.86 | 99.7 |
| | | 40° C./75% RH | Glycolate and free base | 98.52 | 99.3 |
| Fumarate | Initial | NA | NA | 99.46 | NA |
| | 1 week | 25° C./60% RH | No | 99.39 | 99.9 |
| | | 40° C./75% RH | No | 99.15 | 99.7 |
| | 2 weeks | 25° C./60% RH | Fumarate and free base | 99.25 | 99.7 |
| | | 40° C./75% RH | Fumarate and free base | 98.98 | 99.5 |
| Gentisate | Initial | NA | NA | 94.35 | NA |
| | 1 week | 25° C./60% RH | Gentisate and free base | 97.66 | 103.5 |
| | | 40° C./75% RH | Gentisate and free base | 96.89 | 102.7 |
| | 2 weeks | 25° C./60% RH | Gentisate and free base | 97.00 | 102.8 |
| | | 40° C./75% RH | Gentisate and free base | 93.37 | 102.1 |
| Malonate | Initial | NA | NA | 99.45 | NA |
| | 1 week | 25° C./60% RH | Malonate and free base | 99.39 | 99.9 |
| | | 40° C./75% RH | Malonate and free base | 99.14 | 99.7 |
| | 2 weeks | 25° C./60% RH | Malonate and free base | 99.23 | 99.8 |
| | | 40° C./75% RH | Malonate and free base | 97.81 | 98.3 |
| HCl | Initial | NA | NA | 93.94 | NA |
| | 1 week | 25° C./60% RH | No | 97.19 | 103.5 |
| | | 40° C./75% RH | No | 89.25 | 95.0 |
| | 2 weeks | 25° C./60% RH | No | 91.84 | 97.8 |
| | | 40° C./75% RH | No | 84.16 | 89.6 |

TABLE 20-continued

Summary of stability study results

| Salt | Time point | Condition | Form change | Purity (Area %) | Purity vs. initial (%) |
|---|---|---|---|---|---|
| Methanesulfonate | Initial | NA | NA | 91.14 | NA |
| | 1 week | 25° C./60% RH | No | 95.26 | 104.5 |
| | | 40° C./75% RH | No | 88.68 | 97.3 |
| | 2 weeks | 25° C./60% RH | No | 91.95 | 100.9 |
| | | 40° C./75% RH | No | 85.97 | 94.3 |
| Nicotinate | Initial | NA | NA | 97.16 | NA |
| | 1 week | 25° C./60% RH | No | 97.43 | 100.3 |
| | | 40° C./75% RH | No | 97.30 | 100.2 |
| | 2 weeks | 25° C./60% RH | No | 97.45 | 100.3 |
| | | 40° C./75% RH | No | 97.41 | 100.3 |
| Toluenesulfonate | Initial | NA | NA | 96.84 | NA |
| | 1 week | 25° C./60% RH | No | 94.19 | 97.3 |
| | | 40° C./75% RH | No | 89.11 | 92.0 |
| | 2 weeks | 25° C./60% RH | No | 91.40 | 94.4 |
| | | 40° C./75% RH | No | 88.12 | 91.0 |
| Benzenesulfonate | Initial | NA | NA | 90.20 | NA |
| | 1 week | 25° C./60% RH | No | 90.68 | 100.5 |
| | | 40° C./75% RH | No | 82.63 | 91.6 |
| | 2 weeks | 25° C./60% RH | No | 86.37 | 95.8 |
| | | 40° C./75% RH | No | 82.65 | 91.6 |
| Sulfate | Initial | NA | NA | 97.33 | NA |
| | 1 week | 25° C./60% RH | No | 95.22 | 97.8 |
| | | 40° C./75% RH | No | 89.44 | 91.9 |
| | 2 weeks | 25° C./60% RH | No | 93.46 | 96.0 |
| | | 40° C./75% RH | No | 88.20 | 90.6 |

NA = Not applicable;
RH = relative humidity

Example 8. Solubility and Disproportionation of Various Sepiapterin Salts and/or Co-Crystals The kinetic solubility was evaluated for nicotinate, phosphate, L-tartrate, and fumarate salts and/or co-crystals of sepiapterin in water and Medisca Oral Mix. X-ray powder diffraction (XRPD) was performed for the residual solids to identify form change/disproportionation. Solids were suspended into the media with target conc. of ~7 mg/mL (calculated by freebase). The suspensions were agitated on a rolling incubator at 25 rpm for 1, 4 and 24 hrs. At each time point, 1 mL of the suspension was pipetted out for centrifugation at 10000 rpm (2 min) and filtration through 0.45 μm membrane to obtain supernatant for HPLC solubility and pH tests, the residual solids were analyzed by XRPD. The solubility results are summarized in Tables 21-24.

TABLE 21

Solubility summary of nicotinate salt and/or co-crystal

| Media | Time point (hr) | Temp. (° C.) | Solubility (mg/mL)* | Purity (area %)# | Observation | Form change | pH |
|---|---|---|---|---|---|---|---|
| Water | 1 | RT | 1.5 | 98.97 | Turbid | Yes | 2.1 |
| | 4 | | 2.3 | 99.04 | Turbid | Yes | 2.1 |
| | 24 | | 1.8 | 96.54 | Turbid | Yes | 2.1 |
| Medisca Oral Mix | 1 | | 2.6 | 99.76 | Turbid | Yes | 3.1 |
| | 4 | | 3.1 | 99.60 | Turbid | Yes | 3.1 |
| | 24 | | 3.5 | 97.00 | Turbid | Yes | 3.1 |

*Calculated using freebase.
Excess amount of salt sample was dosed for solubility measurement, which may lead to impurity enrichment in supernatant, so the purity data is for reference only.

TABLE 22

Solubility summary of phosphate salt and/or co-crystal

| Media | Time point (hr) | Temp. (° C.) | Solubility (mg/mL)* | Purity (area %)# | Observation | Form change | pH |
|---|---|---|---|---|---|---|---|
| Water | 1 | RT | 1.7 | 89.92 | Turbid | Yes | 2.1 |
| | 4 | | 2.0 | 89.52 | Turbid | Yes | 2.1 |
| | 24 | | 1.9 | 82.64 | Turbid | Yes | 2.1 |
| Medisca Oral Mix | 1 | | 2.5 | 99.23 | Turbid | Yes** | 3.1 |
| | 4 | | 3.2 | 98.95 | Turbid | Yes** | 3.1 |
| | 24 | | 2.1 | 87.63 | Turbid | Yes** | 3.1 |

*Calculated using freebase.
**Low crystallinity.
Excess amount of salt sample was dosed for solubility measurement, which may lead to impurity enrichment in supernatant, so the purity data is for reference only.

TABLE 23

Solubility summary of L-tartrate salt and/or co-crystal

| Media | Time point (hr) | Temp. (° C.) | Solubility (mg/mL)* | Purity (area %)# | Observation | Form change | pH |
|---|---|---|---|---|---|---|---|
| Water | 1 | RT | 1.6 | 99.34 | Turbid | Yes | 2.5 |
| | 4 | | 1.8 | 99.07 | Turbid | Yes | 2.5 |
| | 24 | | 1.8 | 95.61 | Turbid | Yes | 2.5 |
| Medisca Oral Mix | 1 | | 2.0 | 99.68 | Turbid | Yes | 3.3 |
| | 4 | | 2.5 | 99.54 | Turbid | Yes | 3.3 |
| | 24 | | 3.2 | 95.67 | Turbid | Yes | 3.3 |

*Calculated using freebase.
Excess amount of salt sample was dosed for solubility measurement, which may lead to impurity enrichment in supernatant, so the purity data was for reference only.

TABLE 24

Solubility summary of fumarate salt and/or co-crystal

| Media | Time point (hr) | Temp. (° C.) | Solubility (mg/mL)* | Purity (area %)# | Observation | Form change | pH |
|---|---|---|---|---|---|---|---|
| Water | 1 | RT | 1.2 | 98.39 | Turbid | No | 3.1 |
| | 4 | | 1.4 | 98.19 | Turbid | No | 3.1 |
| | 24 | | 1.5 | 95.43 | Turbid | No | 3.1 |

TABLE 24-continued

Solubility summary of fumarate salt and/or co-crystal

| Media | Time point (hr) | Temp. (° C.) | Solubility (mg/mL)* | Purity (area %)# | Observation | Form change | pH |
|---|---|---|---|---|---|---|---|
| Medisca Oral Mix | 1 | | 2.2 | 99.74 | Turbid | No** | 4.0 |
| | 4 | | 3.1 | 99.60 | Turbid | No** | 4.0 |
| | 24 | | 2.9 | 96.54 | Turbid | No** | 4.0 |

*Calculated using freebase.
**Low crystallinity
Excess amount of salt sample was dosed for solubility measurement, which may lead to impurity enrichment in supernatant, so the purity data was for reference only.

Results: For the nicotinate, phosphate, and L-tartrate samples, the residual solids converted to freebase in water and Medisca Oral Mix after 1 hour. For the fumarate sample, no form change was observed for the residual solids in water while the crystallinity of residual solids decreased after 1 hour in Medisca Oral Mix. Surprisingly, of the twelve different salt and/or co-crystal forms studied, the fumarate salt and/or co-crystal was the only salt and/or co-crystal found to have high stability in the solid form stability study of Example 2 and show no evidence of disproportionation in the disproportionation study.

Other Embodiments

It is to be understood that while the present disclosure has been described in conjunction with the detailed description thereof, the foregoing description is intended to illustrate and not limit the scope of the present disclosure, which is defined by the scope of the appended claims. Other aspects, advantages, and alterations are within the scope of the following claims.

What is claimed:

1. A pharmaceutical composition comprising an effective amount of sepiapterin and a pharmaceutically acceptable carrier, wherein the relative amount of antioxidant to sepiapterin is between 0 and 20% wt/wt;
   wherein the antioxidant is ascorbic acid, an ester of ascorbic acid, or a salt of ascorbic acid.

2. The pharmaceutical composition of claim 1, wherein the pharmaceutical composition comprises less than 1.3% of lactoylpterin by weight of the combined amount of sepiapterin and lactoylpterin in the composition.

3. The pharmaceutical composition of claim 1, wherein the pharmaceutical composition is stable at room temperature for at least 6 months.

4. A method of treating phenylketonuria in a subject in need thereof, the method comprising administering to the subject an effective amount of a pharmaceutical composition of claim 1.

5. A method of decreasing phenylalanine levels in a subject in need thereof, the method comprising administering to the subject an effective amount of a pharmaceutical composition of claim 1.

6. A method of treating a tetrahydrobiopterin deficiency in a subject in need thereof, the method comprising administering to the subject an effective amount of a pharmaceutical composition of claim 1.

7. The method of claim 6, wherein the tetrahydrobiopterin deficiency is primary tetrahydrobiopterin deficiency.

8. The pharmaceutical composition of claim 1, formulated as a powder.

9. The pharmaceutical composition of claim 2, formulated as a powder.

10. The pharmaceutical composition of claim 3, formulated as a powder.

11. The pharmaceutical composition of claim 1, wherein the composition further comprises a dispersant selected from crosslinked polyvinylpyrrolidone, carboxymethylcellulose, croscarmellose sodium, starch, or alginic acid, wherein the pharmaceutical composition comprises 0.5-1.5% dispersant by total weight.

12. The pharmaceutical composition of claim 11, wherein the dispersant is croscarmellose sodium, wherein the composition comprises 1% croscarmellose sodium by weight.

13. The pharmaceutical composition of claim 1, wherein the composition further comprises an anti-caking agent or bulking agent selected from colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, and polydimethylsiloxane, wherein the composition comprises about 60-80% anti-caking or bulking agent by total weight.

14. The pharmaceutical composition of claim 13, wherein the anti-caking or bulking agents are microcrystalline cellulose and silicon dioxide, wherein the composition comprises about 63% microcrystalline cellulose by weight and about 6% colloidal silicon dioxide by weight.

15. The pharmaceutical composition of claim 1, wherein the antioxidant is selected from ascorbic acid, ascorbyl palmitate, ascorbyl myristate, ascorbyl stearate, or sodium ascorbate.

16. The pharmaceutical composition of claim 15, wherein the antioxidant is ascorbic acid.

17. The pharmaceutical composition of claim 1, wherein the ratio of sepiapterin to antioxidant is greater than 20:1.

18. The pharmaceutical composition of claim 1, wherein the composition is substantially free of antioxidant.

19. The pharmaceutical composition of claim 1, wherein the pharmaceutical composition comprises about 25% sepiapterin by total weight.

20. The pharmaceutical composition of claim 1, wherein the composition comprises about 25% sepiapterin, about 63% microcrystalline cellulose, about 6% colloidal silicon dioxide, about 1% croscarmellose sodium, and about 5% ascorbic acid.

* * * * *

UNITED STATES PATENT AND TRADEMARK OFFICE
CERTIFICATE OF CORRECTION

PATENT NO. : 11,752,154 B2  
APPLICATION NO. : 16/670362  
DATED : September 12, 2023  
INVENTOR(S) : Daniel E. Levy Page 1 of 1

It is certified that error appears in the above-identified patent and that said Letters Patent is hereby corrected as shown below:

In the Specification

Column 25, Lines 35-41, replace " 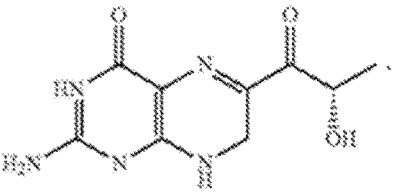 " with

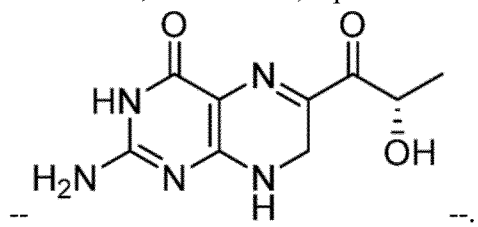

--   --.

Signed and Sealed this  
Seventeenth Day of December, 2024

Derrick Brent  
*Acting Director of the United States Patent and Trademark Office*